(12) United States Patent
Miller et al.

(10) Patent No.: US 10,074,837 B2
(45) Date of Patent: Sep. 11, 2018

(54) INTERFERENCE DETECTION FOR A WIRELESS TRANSFER STATION

(71) Applicant: Enovate Medical, LLC, Murfreesboro, TN (US)

(72) Inventors: David R. Miller, Murfreesboro, TN (US); Mary Metelko, Murfreesboro, TN (US); Allen Kilbourne, Canton, MI (US); Joseph Moody, American Fork, UT (US)

(73) Assignee: Enovate Medical LLC, Murfreesboro, TN (US)

( * ) Notice: Subject to any disclaimer, the term of this patent is extended or adjusted under 35 U.S.C. 154(b) by 739 days.

(21) Appl. No.: 14/323,547

(22) Filed: Jul. 3, 2014

(65) Prior Publication Data

US 2015/0365138 A1    Dec. 17, 2015

Related U.S. Application Data

(60) Provisional application No. 62/010,921, filed on Jun. 11, 2014.

(51) Int. Cl.
  *H02J 17/00* (2006.01)
  *H02J 5/00* (2016.01)
  (Continued)

(52) U.S. Cl.
  CPC ....... *H01M 2/1094* (2013.01); *H01M 2/1022* (2013.01); *H01M 2/1235* (2013.01); *H01M 2/1264* (2013.01); *H01M 2/348* (2013.01); *H01M 10/46* (2013.01); *H01M 10/482* (2013.01); *H01M 10/486* (2013.01); *H01M 10/658* (2015.04); *H01M 10/659* (2015.04); *H02J 5/005* (2013.01); *H02J 7/007* (2013.01); *H02J 7/0021* (2013.01); *H02J 7/0044* (2013.01); *H02J 7/0047* (2013.01); *H02J 7/025* (2013.01); *H02J 17/00* (2013.01); *H02J 50/10* (2016.02); *H02J 50/12* (2016.02); *H02J 50/40* (2016.02); *H02J 50/50* (2016.02); *H02J 50/80* (2016.02); *H04B 5/0037* (2013.01); *H04Q 9/00* (2013.01); *G01V 3/12* (2013.01);
  (Continued)

(58) Field of Classification Search
  None
  See application file for complete search history.

(56) References Cited

U.S. PATENT DOCUMENTS 8,663,106 B2    3/2014  Stivoric et al.
2011/0156494 A1*  6/2011  Mashinsky ............ H02J 17/00
                                                307/104
(Continued)

*Primary Examiner* — Jared Fureman
*Assistant Examiner* — Aqeel Bukhari
(74) *Attorney, Agent, or Firm* — Waller Lansden Dortch & Davis LLP; Matthew C. Cox

(57) ABSTRACT

A technology for a wireless transfer station that is operable to detect interference during a wireless transfer of energy or data between wireless transfer stations. A transfer load on a wireless transfer coil of a wireless transfer station can be monitored during a wireless transfer of energy or data from the wireless transfer station to another wireless transfer station. A change in the transfer load that exceeds a threshold value can be detected. The wireless transfer of energy or data by the wireless transfer station can be adjusted using the wireless transfer coil based on the detected change in the transfer load.

7 Claims, 34 Drawing Sheets

(51) Int. Cl.

| | | |
|---|---|---|
| *H04B 5/00* | (2006.01) |
| *H01M 2/10* | (2006.01) |
| *H02J 7/02* | (2016.01) |
| *H02J 50/12* | (2016.01) |
| *H01M 10/658* | (2014.01) |
| *H01M 10/659* | (2014.01) |
| *H01M 2/12* | (2006.01) |
| *H01M 2/34* | (2006.01) |
| *H01M 10/48* | (2006.01) |
| *H02J 7/00* | (2006.01) |
| *H04Q 9/00* | (2006.01) |
| *H01M 10/46* | (2006.01) |
| *H02J 50/10* | (2016.01) |
| *H02J 50/40* | (2016.01) |
| *H02J 50/80* | (2016.01) |
| *H02J 50/50* | (2016.01) |
| *G01V 3/12* | (2006.01) |

(52) U.S. Cl.
CPC .. *H01M 2200/10* (2013.01); *H01M 2200/103* (2013.01); *H01M 2220/30* (2013.01); *H04B 5/0081* (2013.01); *Y10T 307/469* (2015.04)

(56) References Cited

U.S. PATENT DOCUMENTS

| | | | |
|---|---|---|---|
| 2012/0249051 A1 | 10/2012 | Son et al. | |
| 2013/0026981 A1 | 1/2013 | Van Der Lee | |
| 2013/0117595 A1 | 5/2013 | Murawski et al. | |
| 2013/0241474 A1 | 9/2013 | Moshfeghi | |
| 2014/0001877 A1* | 1/2014 | Stevens | H02J 5/005 307/104 |
| 2014/0002014 A1 | 1/2014 | Sultenfuss et al. | |
| 2014/0056286 A1* | 2/2014 | Nagata | H04W 74/0808 370/336 |
| 2014/0340031 A1* | 11/2014 | Mi | H04B 5/0037 320/108 |
| 2015/0015086 A1* | 1/2015 | Krammer | B60L 11/182 307/104 |

* cited by examiner

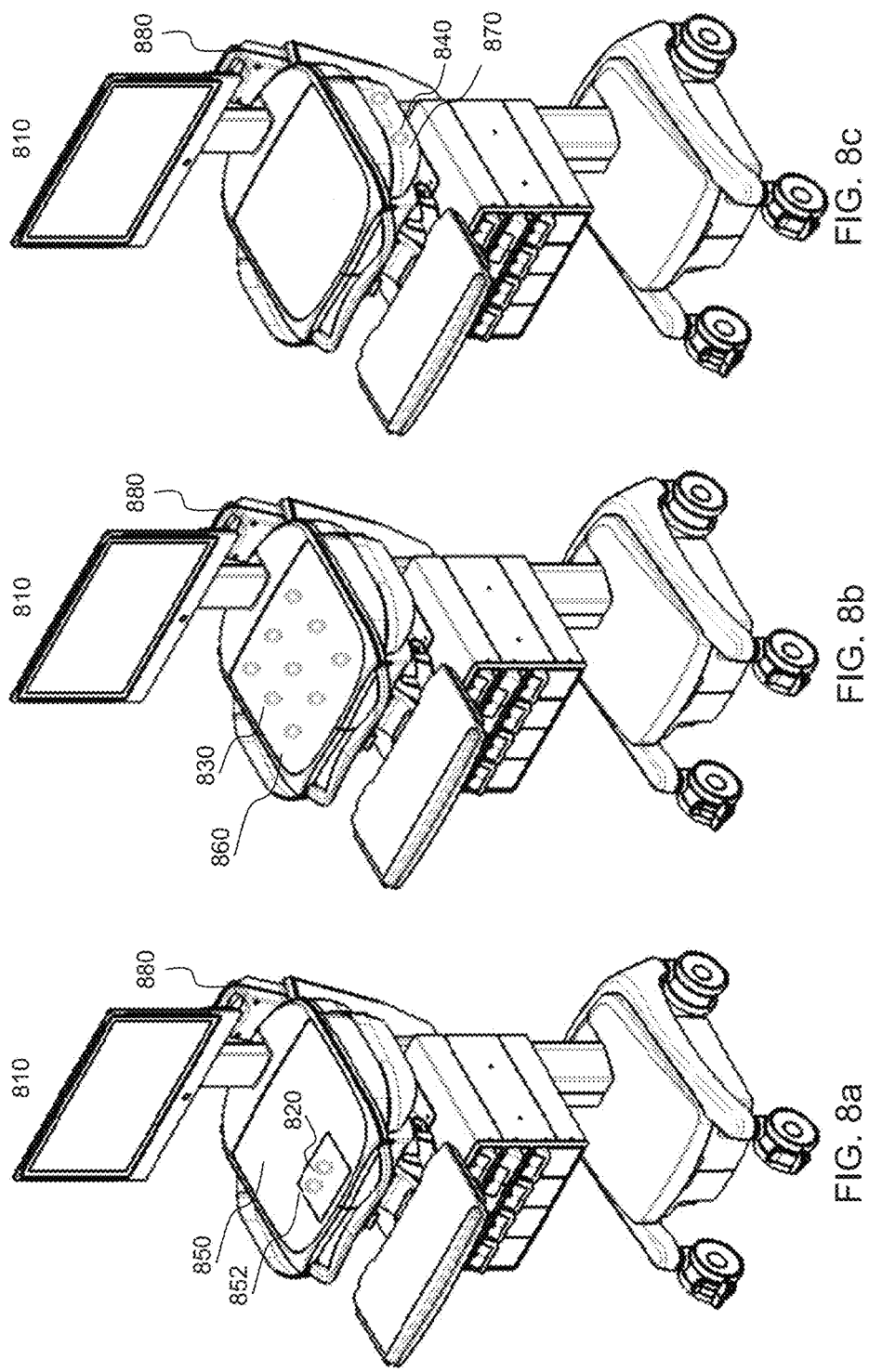

INTERFERENCE DETECTION FOR A WIRELESS TRANSFER STATION

This application claims the benefit of and hereby incorporates by reference U.S. Provisional Patent Application Ser. No. 62/010,921, filed Jun. 11, 2014.

BACKGROUND

Wireless energy transfer is a transfer of electrical energy from an energy source to an electrical load without interconnecting wires. Wireless energy transfer is useful in cases where interconnecting wires or physical electric contacts are inconvenient, hazardous, or not plausible. Wireless energy transfer occurs when a transmitting coil generates a magnetic field and a receiving coil is located within that field so that a current is induced at the receiving coil, i.e. a transmitting coil coupled to a receiving coil.

When the transmitting coil couples with the receiving coil, energy from the transmitting coil can be wirelessly transferred to the receiving coil over a distance. While wireless energy transfer is intended to occur between the transmission coil and the receiving coil, when a foreign object, such as an electrically conductive object, that is not part of the wireless energy transfer system is located within the magnetic field emitted from the transmission coil, the object can inadvertently couple with the magnetic field emitted by the transmitting coil and receive at least a portion of the wireless energy transfer.

The foreign object receiving at least a portion of the wireless energy transfer causes energy wastage and a reduction in efficiency. In addition to the energy wastage and reduction in efficiency, coupling of the foreign object with the magnetic field can also cause the foreign object to radiate the received energy in the form of heat. The radiation of heat from the foreign object can damage adjacent devices or pose a safety threat. Object presence detection and interference detection can reduce energy wastage and reduce safety risks.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein:

FIG. 8a depicts a wheeled medical cart with a plurality of wireless transfer stations integrated into a selected area of a work surface of the wheeled medical cart in accordance with an example;

FIG. 8b depicts a wheeled medical cart with a plurality of wireless transfer stations integrated into a work surface of the wheeled medical cart in accordance with an example;

FIG. 8c depicts a wheeled medical cart with one or more of wireless transfer stations integrated into a device holder of the wheeled medical cart in accordance with an example;

Figure 1:
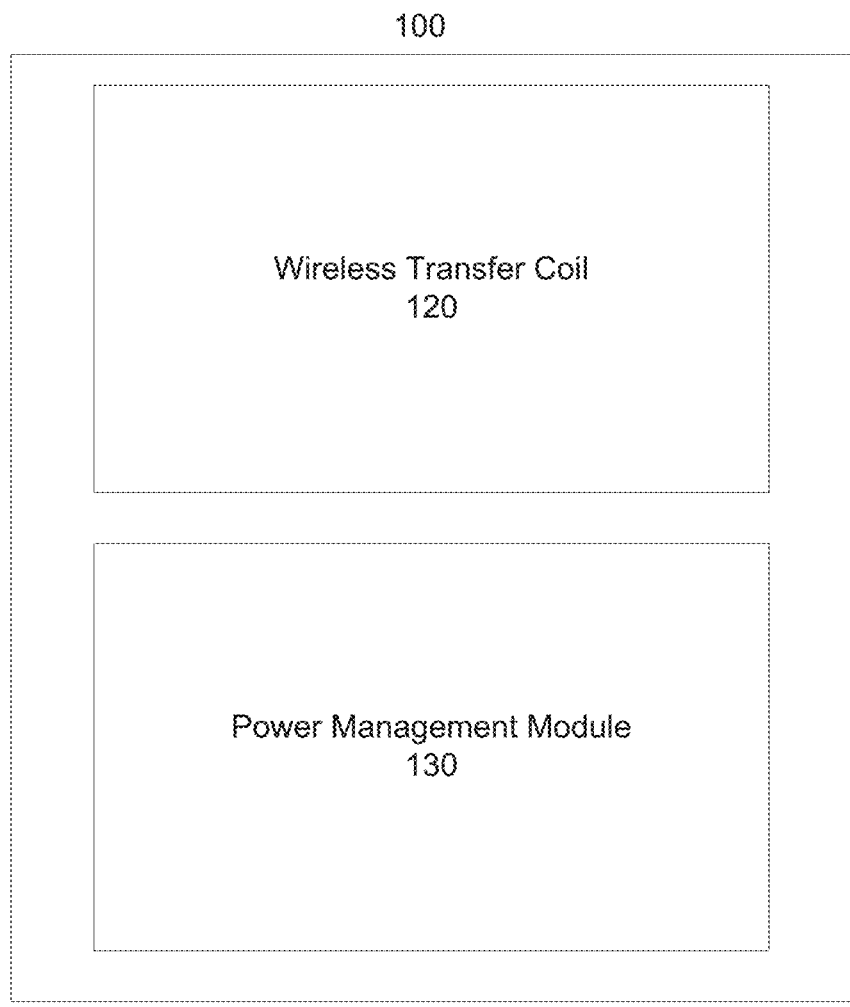
FIG. 1 depicts a wireless transfer station in accordance with an example.

Reference will now be made to the exemplary embodiments illustrated, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence.

The terms battery, cell, and/or battery cell as used herein can be used interchangeably and can refer to any of a variety of different cell chemistries and configurations. In one embodiment the cell chemistries and configurations can include, but are not limited to, lithium ion (e.g., lithium iron phosphate, lithium cobalt oxide, other lithium metal oxides, etc.), lithium ion polymer, nickel metal hydride, nickel cadmium, nickel hydrogen, nickel zinc, silver zinc, or other battery type/configurations.

The term battery pack as used herein can refer to one or more individual batteries contained within a single piece housing, or a multiple piece housing. The one or more individual batteries can be electrically interconnected in parallel and/or in series to achieve a selected energy level (such as a voltage level or a current level) and capacity level.

An increasing number and variety of electronic devices are powered using non-wired energy sources, such as batteries or wireless energy sources that provide power directly to the device or to energy storage systems. The electronic devices can range from mobile phones, portable music players, laptop computers, and tablet computers to medical devices such as hearing aids, pace makers, wheeled medical carts, medical measurement equipment, medical test equipment, and other types of medical equipment.

Traditionally, battery chargers operate to charge one or more batteries by either simultaneously charging one or more batteries of the same type using a single charging port or by charging each of the batteries of the same type simultaneously using multiple charging ports. Traditional battery chargers can only recharge one type of battery and do not account for individual characteristics of different types of batteries. The battery chargers are often limited in the type of battery they can recharge. In one example, a traditional battery charger can only provide a fixed voltage output and a fixed current output to a selected battery or type of battery with a selected energy level. Energy level in batteries are typically measured in watt-hours or amp-hours.

Often, rechargeable batteries are used as a replenishable energy source for electronic devices. In one embodiment, a battery pack can include one or more rechargeable batteries. In one example, the one or more rechargeable batteries can be a lead-based battery, a lithium-based battery, a nickel based battery, or another type of chemical storage battery. Traditionally, a rechargeable battery pack provides energy to an electronic device using physical electrically conductive connections between the rechargeable battery pack and the electronic device. When the traditional rechargeable batteries of the rechargeable battery pack are depleted, the rechargeable batteries can be replenished by connecting physical electrically conductive contacts between the rechargeable battery pack and a battery charger.

In one embodiment of the present invention, a wireless transfer station can receive energy and/or send energy to another device, such as another wireless transfer station, using a wireless energy transfer scheme (e.g. transfer energy without wires). A wireless energy transfer scheme can be any form of wireless energy transfer associated with the use of electric fields, magnetic fields, electromagnetic fields, and so forth that allows electrical energy to be transmitted between two or more wireless transfer elements without using physical electrical contacts. In one example, a wireless energy transfer of wireless energy can be a transfer of electrical energy from an energy source to an electrical load without the use of interconnecting wires or physical electrical contacts.

In one embodiment, the wireless transfer station can include one or more wireless transfer coils to transfer energy and/or data with other wireless transfer stations. The wireless transfer coil can include one or more power management modules to control the energy transfers and/or data transfers with the other wireless transfer stations.

Examples of a wireless transfer station includes a wireless energy rechargeable battery pack, a wireless energy transfer platform and/or data transceiver integrated into a medical cart, a wireless energy transfer platform and/or data transceiver integrated into an electronic device, a wireless energy transfer platform and/or data transceiver integrated into a piece of furniture, a wireless energy transfer platform and/or data transceiver integrated into a plate mounted to a wall, a wireless energy transfer platform and/or data transceiver integrated into a device (such as a medical device or medical equipment), and so forth.

In one example, the wireless transfer station can be a wireless energy battery pack that can be attached to a device, such as a medical cart or medical equipment. The wireless transfer station that transfers energy and/or data with the device can also relay the energy and/or data with other devices and/or wireless transfer stations. These examples are not intended to be limiting. The wireless transfer station can be implemented in a variety of electronic devices and mounting locations.

In one embodiment, the wireless transfer station can receive data from and/or send data or information to another device, such as another wireless transfer station, using a wireless data transfer scheme. In another embodiment, the wireless data transfer scheme can be any form of data transfer associated with a communications network. In another embodiment, the communications network can be a cellular network. The cellular network can be configured to operate based on a cellular standard, such as the third generation partnership projection (3GPP) long term evolution (LTE) Rel. 8, 9, 10, 11, or 12 standard, or the institute of electronic and electrical engineers (IEEE) 802.16p, 802.16n, 802.16m-2011, 802.16h-2010, 802.16j-2009, or 802.16-2009 standard.

In another embodiment, the communications network can be a wireless local area network (such as a wireless fidelity network (Wi-Fi)) that can be configured to operate using a standard such as the IEEE 802.11-2012, IEEE 802.11ac, or IEEE 802.11ad standard. In another embodiment, the communications network can be configured to operate using a Bluetooth standard such as Bluetooth v1.0, Bluetooth v2.0, Bluetooth v3.0, or Bluetooth v4.0. In another embodiment, the communications network can be configured to operate using a ZigBee standard, such as the IEEE 802.15.4-2003 (ZigBee 2003), IEEE 802.15.4-2006 (ZigBee 2006), or IEEE 802.15.4-2007 (ZigBee Pro) standard. In another embodiment, the wireless data transfer scheme can be any form of data transfer associated with electric fields, magnetic fields, or electromagnetic fields that is transmitted between two or more wireless transfer elements without using physical electrical contacts.

In one embodiment, the wireless transfer station can include one or more wireless transfer elements. In one example, a wireless transfer element can be a wireless transfer coil. In one embodiment, the wireless transfer coil can be a coil used for transmitting and/or receiving energy and/or data using magnetic inductance and/or magnetic resonance.

FIG. 1 illustrates a wireless transfer station 110. FIG. 1 further illustrates that the wireless transfer station 110 can include a wireless transfer coil 120 and a power management module 130. In one example, the power management module 130 can convert energy received from an energy source, such as another wireless transfer station or an alternating current (AC) energy outlet, a selected current level, a selected voltage level, and/or a selected wattage level. In another embodiment, the wireless transfer station 110 can include one or more batteries, such as rechargeable batteries. In one embodiment, the wireless transfer coil 120 can comprise a transmitting coil and/or a receiving coil.

Figure 2:
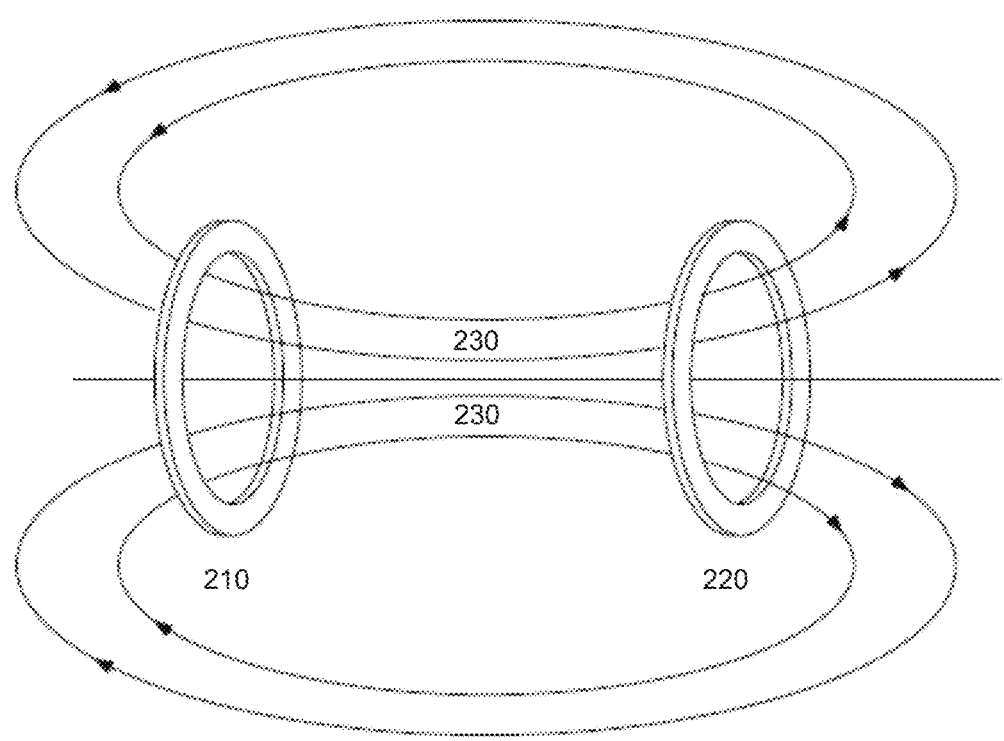
FIG. 2 depicts transferring energy or data between a plurality of wireless transfer coils in accordance with an example.

FIG. 2 illustrates an example of transferring energy or data between a plurality of wireless transfer coils 210 and 220. FIG. 2 further illustrates that one of the plurality of wireless transfer coils 210 can be a transmitting coil 210 and another one of the plurality of wireless transfer coils 220 can be a receiving coil 220. In one embodiment, energy and/or data can be transferred from the transmitting coil 210 to the receiving coil 220 by coupling the transmitting coil 210 with the receiving coil 220 to enable the energy or data to be transferred over a gap or distance. In one example, wireless energy can be transferred by generating a magnetic field 230 (such as an electromagnetic field) at the transmitting coil 210 and positioning the receiving coil 220 within the magnetic field 230 to induce a current at the receiving coil 220.

The process of inducing a current at the receiving coil is referred to as coupling the receiving coil 220 to the transmitting coil 210. In one embodiment, the wireless transfer coil coupling for wireless energy or data transfer can be a magnetic induction coupling. In another embodiment, the wireless transfer coil coupling for wireless energy transfer can be a magnetic resonant coupling.

In one embodiment, the transmitting coil 210 can be a transmitting induction coil and the receiving coil 220 can be a receiving induction coil. The wireless transfer station can use a magnetic field to transfer energy between the transmitting coil 210 coupled to a first object (such as a wireless transfer station) and a receiving coil 220 of a second object (such as another wireless transfer station) without any direct contact between the transmitting coil 210 and the receiving coil 220, e.g. inductive coupling.

In one embodiment, inductive coupling can occur when the transmitting coil 210 creates a magnetic field 230 (such as an alternating electromagnetic field) using an energy source, such as an alternating current (AC) energy outlet or a direct current (DC) battery. A current can be induced at the receiving coil 220 using the magnetic field when the receiving coil 220 is located within the magnetic field 230.

In one example, when the transmitting coil 210 and the receiving coil 220 are within a threshold proximity distance, the transmitting coil 210 and the receiving coil 220 can couple to form an electric transformer. In one embodiment, current from the receiving coil 220 can be transferred to a battery or an electronic device. In another embodiment, the current can be stored in one or more energy sources of the wireless transfer station, such as a battery. In another embodiment, the current can be transferred to a device coupled to the wireless transfer station. In one embodiment, an impedance of one or more transmitting coils 210 can be substantially matched with an impedance of one or more receiving coils 220.

In one embodiment, the transmitting coil 210 can be a transmitting resonant coil and the receiving coil 220 can be a receiving resonant coil. A wireless resonant transfer can be a resonant transmission of energy or data between at least one transmitting coil 210 and at least one receiving coil 220. In another embodiment, at least one transmitting coil 210 and at least one receiving coil 220 can be tuned to resonate at a same frequency or a substantially same frequency.

In one example, resonant transmission of wireless energy can occur when the transmitting coil and the receiving coil are constructed to resonate at the same frequency or approximately the same frequency. The transmitting coil 210 can be configured to oscillate current at the resonant frequency of the coils to transfer energy and/or data. The oscillating current of the transmitting coil 210 can generate an oscillating magnetic field at the selected resonant frequency of the receiving coil. When the receiving coil 220 is positioned adjacent to the oscillating magnetic field and constructed to operate at the same frequency or substantially the same frequency as the transmitting coil 210, the receiving coil 220 can receive energy and/or data from the oscillating magnetic field.

In another embodiment, an impedance of one or more transmitting coils 210 can be substantially matched with an impedance of one or more receiving coils 220 for energy and/or data transfer. In another embodiment, the transmitting coil and the receiving coil can be positioned such that the receiving coil is within the near field of the magnetic field of the transmitting coil. The near field can be based within the Fraunhofer region, which can be approximately within $\frac{1}{2}\pi$ times the wavelength of the electromagnetic field.

One advantage of placing the receiving coil within the near field for wireless energy transfer is to reduce an amount of energy that may be radiated or leaked from the wireless transfer coils 210 and 220, e.g. energy not received at the receiving coil 220. In one embodiment, energy in a magnetic field falls off as the inverse squared of a distance ($1/d^2$) between the transmitting coil 210 and the receiving coil 220 within the near field. In one example, magnetic resonant coupling can be used to transfer energy at relatively high energy levels between the transmitting coil 210 and the receiving coil 220 and to minimize or reduce energy leaking away from the wireless transfer coils 210 and 220.

Another advantage of using a near field or a non-radiating field for wireless energy transfer can be that the near field or the non-radiating field can be used in areas adjacent to biological material, such as humans or other biological entities, with minimal or no effects to the biological material from the wireless energy transfer. In another embodiment, a wireless transfer station, such as in FIG. 1, can use a radio frequency (RF) signal, ultrasound, and/or laser beams to wirelessly transfer energy and/or data between a transmitting device and a receiving device.

Figure 3A:
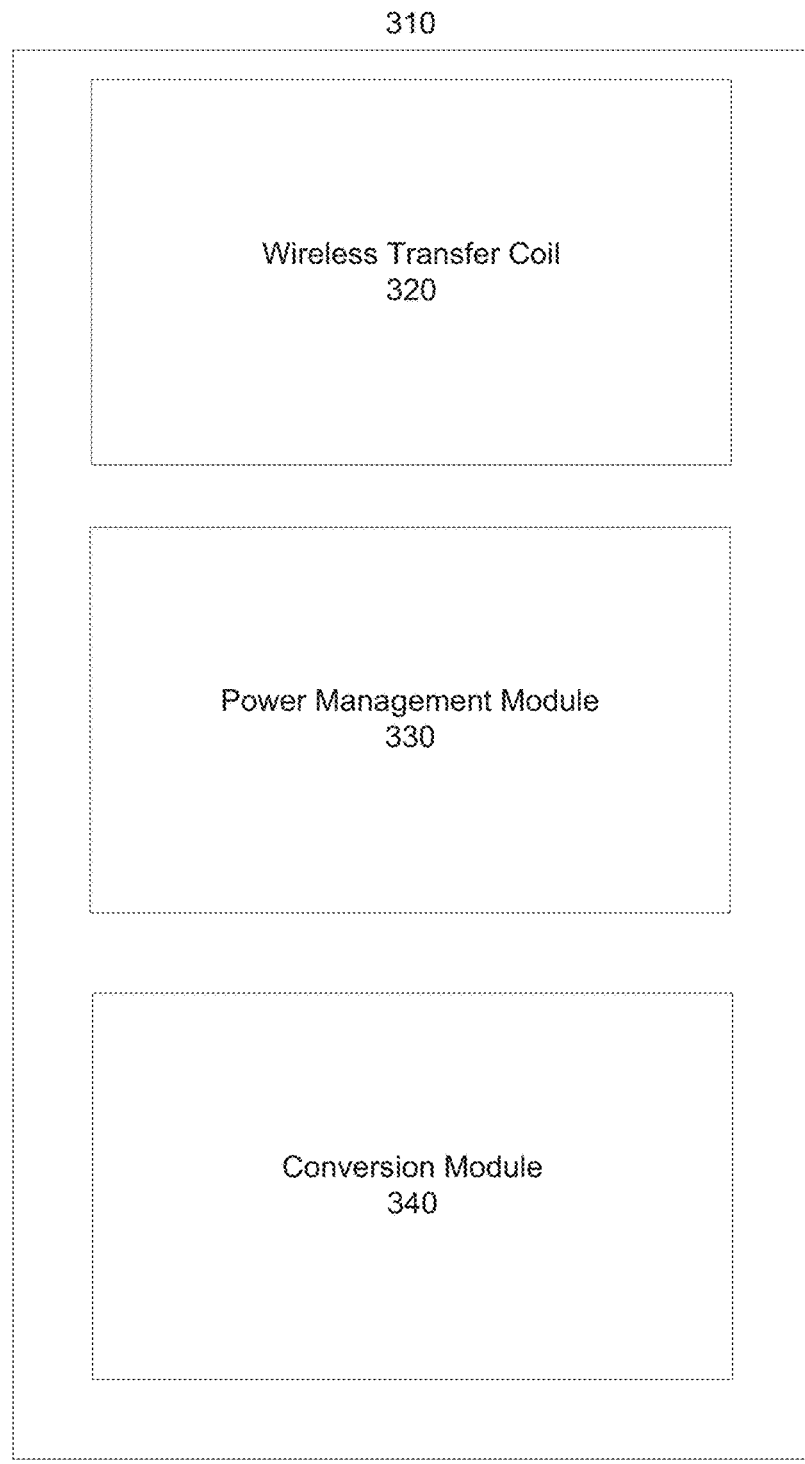
FIG. 3a depicts a wireless transfer station in accordance with an example.

FIG. 3a shows a wireless transfer station 310 that can include: a wireless transfer coil 320, a power management module 330, and a conversion module 340. In one embodiment, the wireless transfer coil 320 can be used for resonance coupling and/or induction coupling. In one example, the conversion module 340 can be coupled to the wireless transfer coil 320 and used to switch the wireless transfer coil 320 from a resonance mode (i.e. transferring wireless energy and/or data using magnetic resonance coupling) to an induction mode (i.e. transferring wireless energy and/or data using magnetic induction coupling), or vice versa.

In one embodiment, the wireless transfer coil 320 of the wireless transfer station 310 can be used for transmitting wireless energy and/or receiving wireless energy. In one example, the conversion module 340 can be coupled to the wireless transfer coil 320 and used to switch the wireless transfer coil 320 from a receiving mode (i.e. receiving wireless energy and/or data) to a transmitting mode (i.e. transmitting wireless energy and/or data), or vice versa.

In one embodiment, when the conversion module 340 of the wireless transfer station 310 is in the transmitting mode, the conversion module 340 or the power management module 330 can convert energy received from an energy source (such as a power outlet or a battery) at a selected voltage into a high frequency alternating current and transmit the high frequency alternating current to a wireless transfer coil of another wireless transfer station. The high frequency alternating current can flow through one or more loops of the wireless transfer coil 320 and create a varying magnetic field that can induce a current in the other wireless transfer coil. In another embodiment, when the conversion module 340 is switched to the receiving mode, a varying magnetic field from another wireless transfer station can induce an alternating current flowing through the one or more loops of the wireless transfer coil 320. The current flowing through the one or more loops can be converted into a direct current (DC) by the conversion module 340 or the power management module 330 and directed to a battery coupled to the wireless transfer station 310 or a device that is electrically coupled to the wireless transfer station 310.

In one embodiment, each wireless transfer coil 320 of a wireless transfer station 310 can be coupled to a separate conversion module 340. In another embodiment, one or more conversion modules 340 can be coupled to one or more selected groups of wireless transfer coils 320. One advantage of using a conversion module 340 for switching a wireless transfer coil 320 between transmitting mode and receiving mode can be to reduce a complexity of design and/or size of a wireless transfer station 310 by reducing a number of wireless transfer coils 320 used to transmit and/or receive wireless energy. Another advantage of using a conversion module 340 for switching a wireless transfer coil between a transmitting mode and receiving mode is to provide a dual functionality to a wireless transfer station of both transmitting and receiving wireless energy.

Figure 3B:
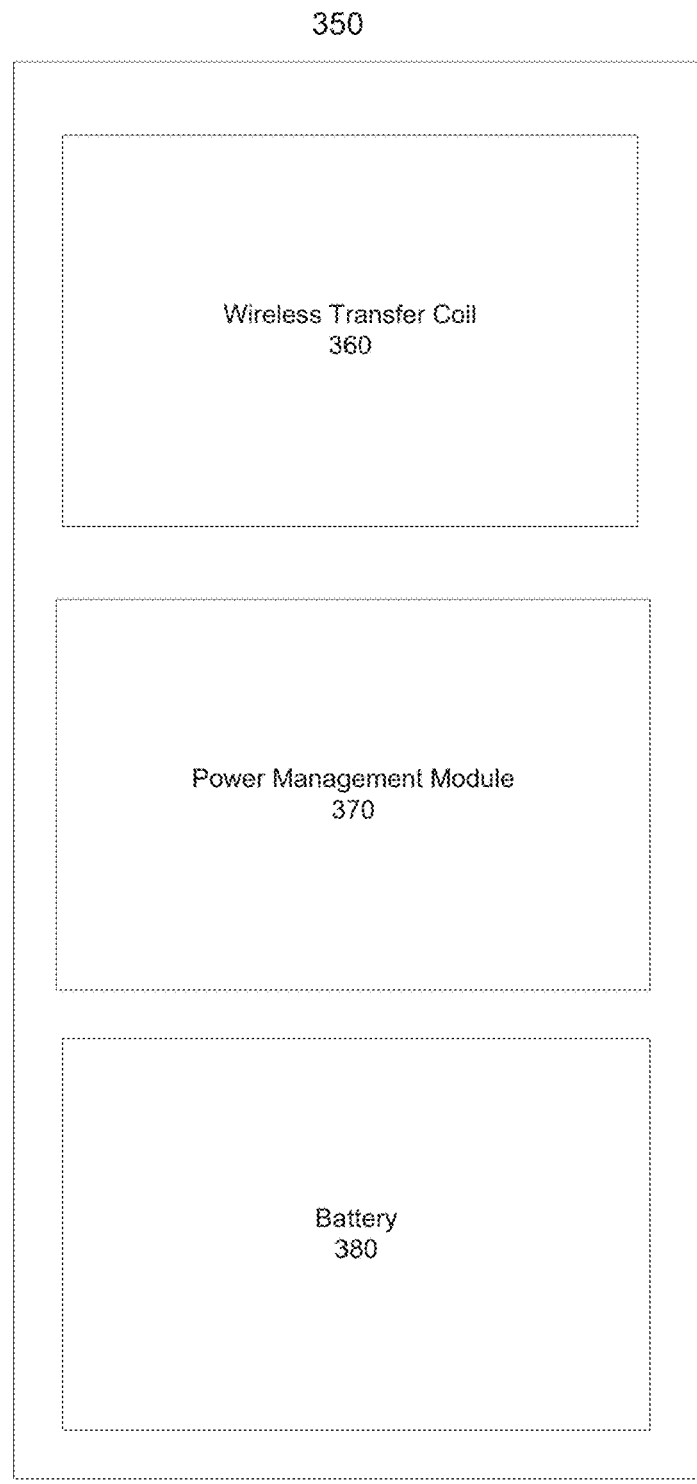
FIG. 3b depicts another wireless transfer station in accordance with an example.

FIG. 3b illustrates a wireless transfer station 350. FIG. 3b further illustrates that the wireless transfer station 350 can include: a wireless transfer coil 360; a power management module 370; and a battery 380. The battery 380 can comprise a plurality of batteries, such as rechargeable batteries. In one example, the power management module 370 can convert energy received using the wireless transfer coil 360 from an energy source, such as another wireless transfer station or an alternating current (AC) energy outlet, to a selected current level at a selected voltage level to provide a selected wattage level. In one embodiment, the power management module can transfer the converted energy to the battery 380 to store the energy.

Figure 3C:
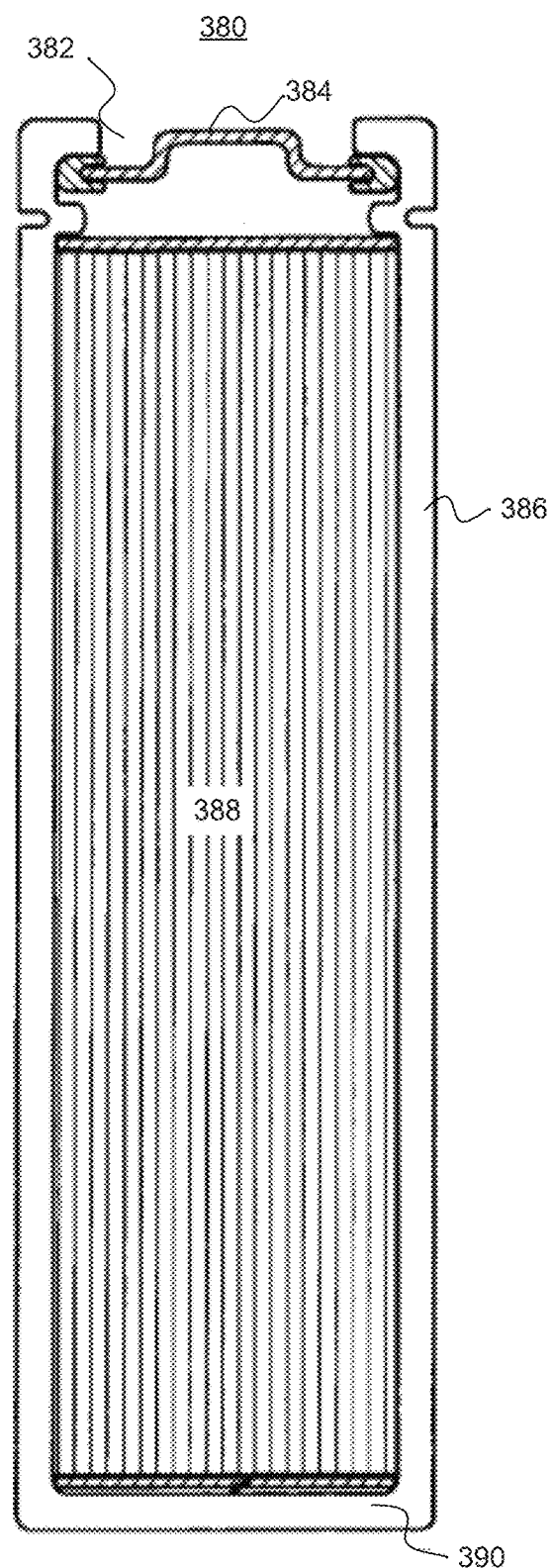
FIG. 3c depicts a cross-sectional view of a battery in accordance with an example.

FIG. 3c shows a cross-sectional view of a battery 380, for example a lithium ion battery utilizing an 18650 battery form-factor. The battery 380 can include: a case 386, such as a cylindrical case; one or more electrodes 388, and a cap 384. In one embodiment, the case 386 can be made of a metal, such as nickel-plated steel, that can be non-reactive with battery materials, such as an electrolyte or the one or more electrodes 388. In one embodiment, a bottom surface 390 of the case 386 can be seamlessly integrated with the remainder of the case 386. In one embodiment, a top end 382 of the case 386 can be open ended. In another embodiment, the cap 384 can be located at the top end 382 of the case 386. In another embodiment, the top end 382 can be a positive electrical terminal of the battery 380 and the bottom end 390 can be a negative electrical terminal. In one example, the positive electrical terminal and the negative electrical terminal of the battery 380 can be connected to a wireless transfer station to provide energy to the wireless transfer station. In another embodiment, a plurality of batteries can be connected in series and/or in parallel. In one embodiment, the battery 380 can be connected to a power management module, such as the power management modules in FIGS. 3a and 3b.

Figure 4:
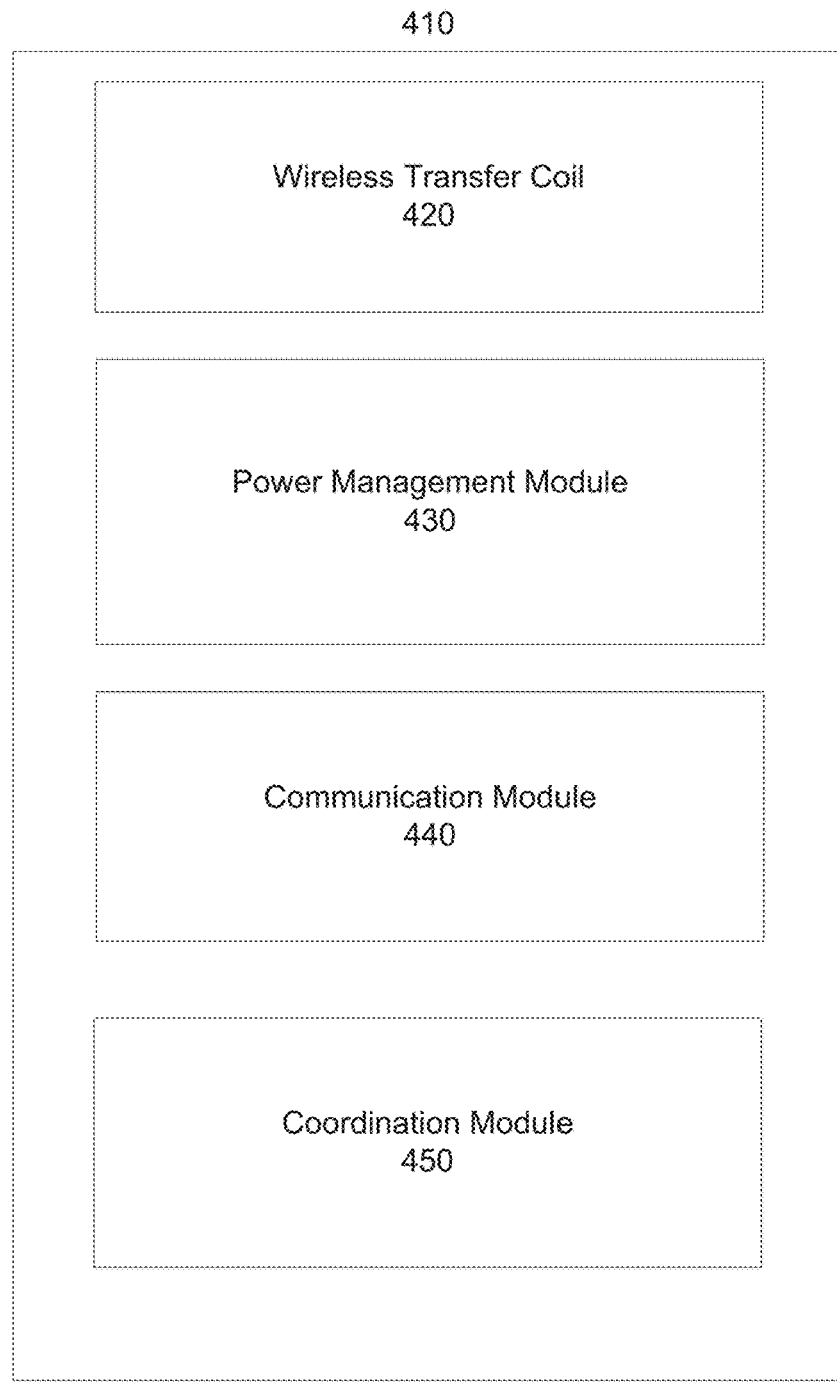
FIG. 4 depicts a wireless transfer station in accordance with an example.

FIG. 4 shows a wireless transfer station 410 that can include: a wireless transfer coil 420, a power management module 430, a communications module 440, and/or a coordination module 450. In one embodiment, the wireless transfer station 410 can communicate with one or more other wireless transfer stations or one or more devices using the communication module 440.

In one embodiment, the communication module 440 of the wireless transfer station 410 can use a communications network to communicate the data to a device and/or another wireless transfer station. In another embodiment, the communications network can be a cellular network that may be a 3GPP LTE Rel. 8, 9, 10, 11, or 12 or IEEE 802.16p, 802.16n, 802.16m-2011, 802.16h-2010, 802.16j-2009, 802.16-2009. In another embodiment, communications network can be a wireless network (such as a wireless fidelity network (Wi-Fi)) that may follow a standard such as the Institute of Electronics and Electrical Engineers (IEEE) 802.11-2012, IEEE 802.11ac, or IEEE 802.11ad standard. In another embodiment, the communications network can be a Bluetooth connection such as Bluetooth v1.0, Bluetooth v2.0, Bluetooth v3.0, or Bluetooth v4.0. In another embodiment, the communications network can be a ZigBee connection such as IEEE 802.15.4-2003 (ZigBee 2003), IEEE 802.15.4-2006 (ZigBee 2006), IEEE 802.15.4-2007 (ZigBee Pro).

In one embodiment, the wireless transfer station 410 can transfer energy to one or more other wireless transfer stations, receive energy from one or more other wireless transfer stations, and/or communicate data or information with one or more other wireless transfer stations. In another embodiment, the coordination module 450 of the wireless transfer station 410 can coordinate when energy is transferred between wireless transfer stations and/or when data is communicated between wireless transfer stations. In another embodiment, the coordination module 450 can use the communications module 440 to communicate with one or more other wireless transfer stations to coordinate energy and/or data transfer between the wireless transfer station 410 and the one or more other wireless transfer stations.

One advantage of transferring energy and/or data using a wireless transfer station 410 is to provide a single connection point between the wireless transfer station 410 and other wireless transfer stations and/or other devices. Another advantage of transferring energy and/or data using the wireless transfer station 410 can be to enable a single step for both transferring energy between the wireless transfer station 410 and other wireless transfer stations and communicating or synchronizing data communicated between the wireless transfer station 410 and other wireless transfer stations. In one example, when a first wireless transfer station (such as a wireless transfer station integrated into a medical cart) is located adjacent to a second wireless transfer station (such as a wireless transfer station integrated into a plate mounted to a wall or a floor mat), the first wireless transfer station can both receive energy from the second wireless transfer station and synchronize information with the second wireless transfer station.

In one embodiment, the coordination module 450 can communicate with a conversion module, as in FIG. 3a, to coordinate when one or more wireless transfer coils 420 of the wireless transfer station 410 can transmit and/or receive wireless energy and/or data. In one example, the coordination module 450 communicates with a conversion module, as in FIG. 3a, to coordinate transmitting and/or receiving wireless energy and/or data by coordinating when one or more wireless transfer coils 420 are in a transmitting mode or a receiving mode, as discussed in the preceding paragraphs.

Figure 5A:
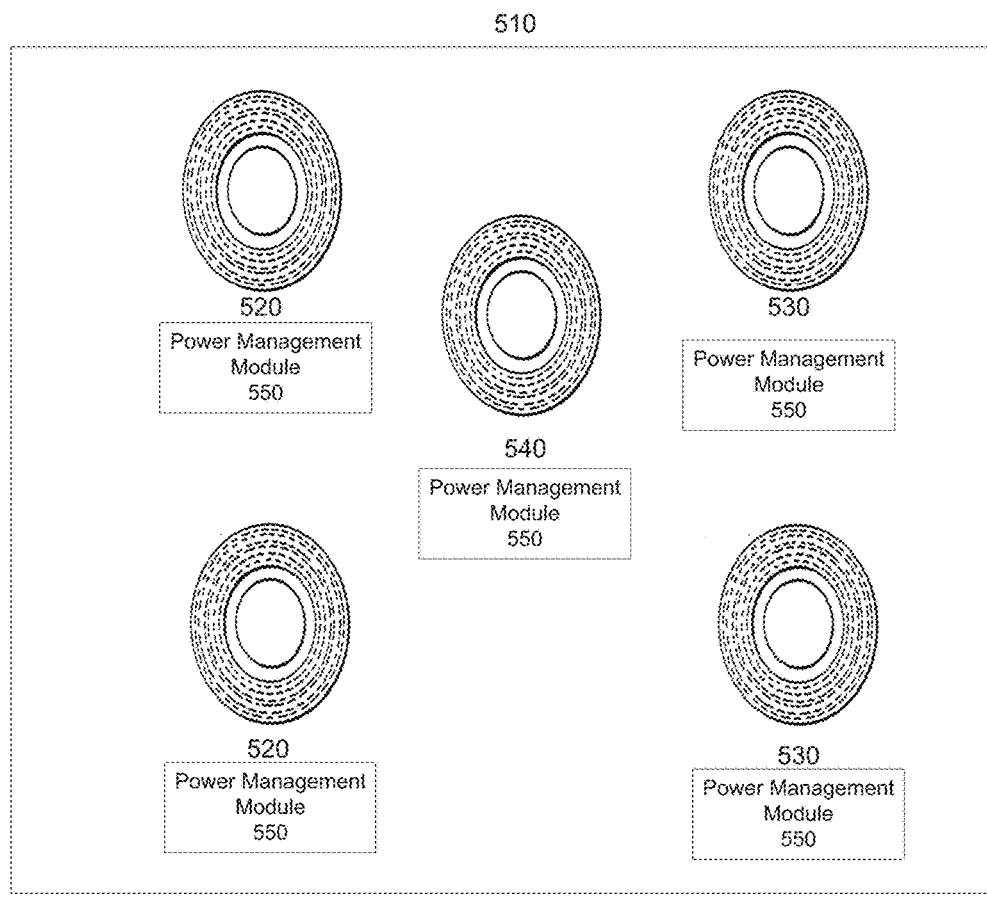
FIG. 5a depicts a wireless transfer station that includes one or more resonant wireless transfer coils and/or one or more induction wireless transfer coils in accordance with an example.

FIG. 5a shows a wireless transfer station 510 that includes one or more resonant wireless transfer coils 520 and/or one or more induction wireless transfer coils 530. In one example, the wireless transfer station 510 can have a resonant wireless transfer coil 520 and can transfer energy to a resonant wireless transfer coil of a first wireless transfer station and can have an induction wireless transfer coil 530 and can transfer energy to an induction wireless transfer coil of a second wireless transfer station. One advantage of the wireless transfer station having both resonant wireless transfer coils 520 and induction wireless transfer coils 530 can be to provide energy and/or data to wireless transfer stations and/or devices with only one of the resonant wireless transfer coils or the induction wireless transfer coils, thereby enabling more devices to transfer energy to the wireless transfer station.

In one embodiment, a device or another wireless transfer station can include one or more resonant wireless transfer coils and/or one or more induction wireless transfer coils. In one embodiment, the device or the other wireless transfer station receiving energy from the wireless transfer station 510 can select whether to receive wireless energy from the one or more resonant wireless transfer coils 520 or the one or more induction wireless transfer coils 530 of the wireless transfer station 510. In another embodiment, the wireless transfer station 510 can be configured to select whether to transmit wireless energy using the one or more resonant wireless transfer coils 520 or the one or more induction wireless transfer coils 530. In one example, a resonant transmitting coil and a resonant receiving coil pair can have a higher energy transfer efficiency than an induction transmitting coil and an induction receiving coil pair. In this example, when the device or the other wireless transfer station includes a resonant receiving coil, the other wireless transfer station and/or the device or the wireless transfer station 510 can be configured to use one or more resonant wireless transfer coils to perform an energy transfer.

In one embodiment, the one or more resonant wireless transfer coils 520 and/or the one or more induction wireless transfer coils 530 can be transmitting coils and/or receiving coils. In another embodiment, the wireless transfer station 510 can include one or more repeater coils 540. In one example, the repeater coil 540 can enhance wirelessly transmitted energy of a transmitting coil, e.g. providing additional transmission energy. In another example, the repeater coil 540 can receive the wireless energy from a transmitting coil and relay or retransmit the received energy to another repeater coil 540 or to a receiving coil. The repeater coils can be configured as inductive repeater coils or resonant repeater coils, and associated with transmit coils and receive coils of the same kind.

In one embodiment, the one or more resonant wireless transfer coils 520, the one or more induction wireless transfer coils 530, and/or the repeater coil 540 can include a power management module 550 configured to covert energy from an energy source to a varying magnetic field. In another embodiment, the one or more resonant wireless transfer coils 520, the one or more induction wireless transfer coils 530, and/or the repeater coil 540 can be coupled to a power management module 550 configured to convert a magnetic field into energy, such as energy at a selected current level, a voltage level, a wattage level, and/or an amperage level, and transfer the energy to a battery of the wireless transfer station 510 or a device coupled to the wireless transfer station 510.

Figure 5B:
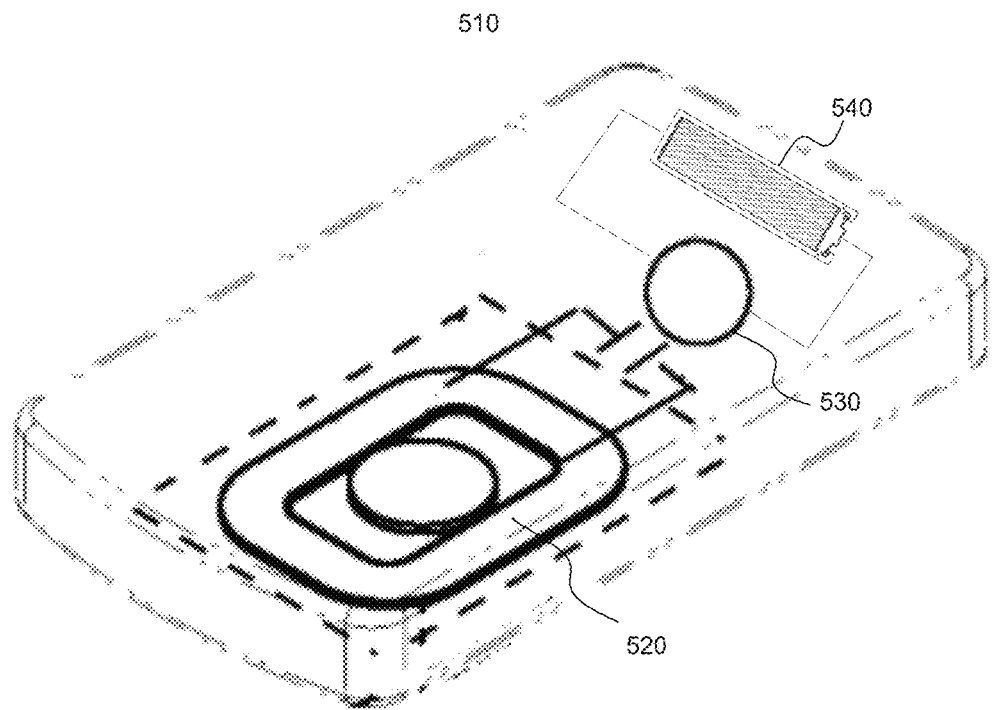
FIG. 5b depicts a wireless transfer station in accordance with an example.

FIG. 5b illustrates one exemplary embodiment of the wireless transfer station 510. In one embodiment, the wireless transfer station 510 can be a stand-alone device used to transfer wireless energy to other devices. In another embodiment, the wireless transfer station 510 can include a wireless transfer coil 520 and a power management module 530. In another embodiment, the wireless transfer station 510 can direct energy received at the wireless transfer coil 520 using the power management module 530 to a device coupled to the wireless transfer station 510.

In another embodiment, the wireless transfer station 510 can transfer the energy received at the wireless transfer coil 520 to the coupled device using physical electrical contacts. In another embodiment, the wireless transfer station 510 can transfer the energy to the coupled device using the wireless transfer coil 520. In one embodiment, the wireless transfer station 510 can store received energy at a battery 540.

Figure 5C:
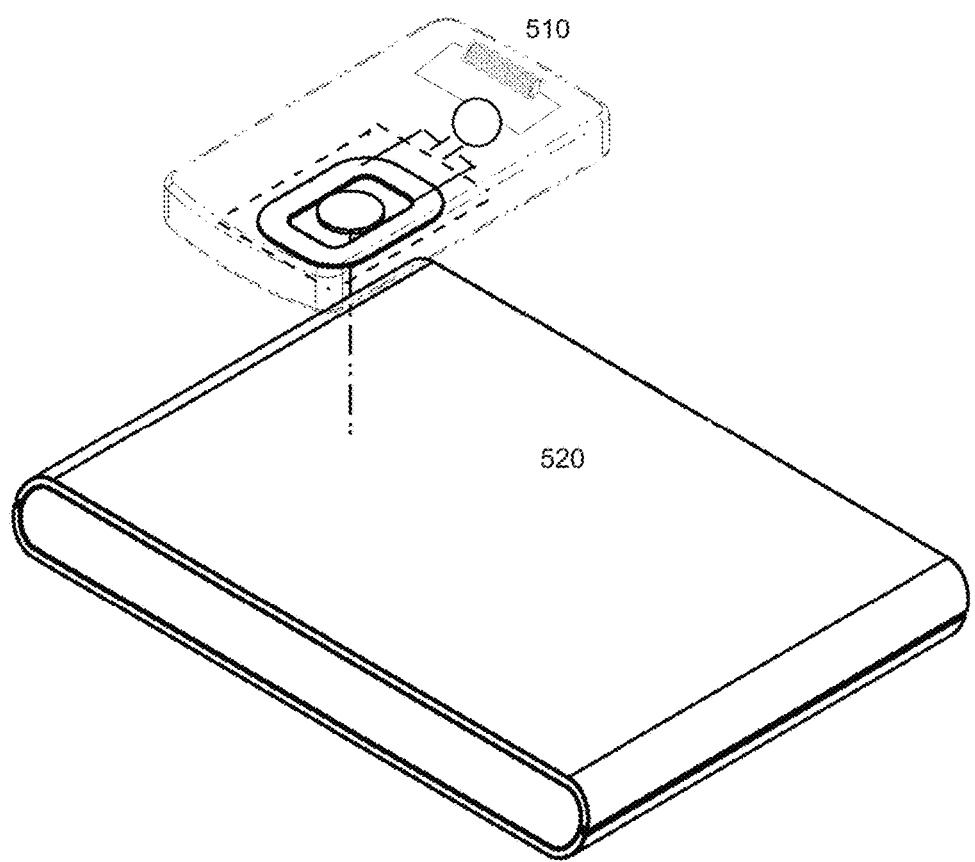
FIG. 5c depicts a wireless transfer station integrated into an object in accordance with an example.
Figure 5D:
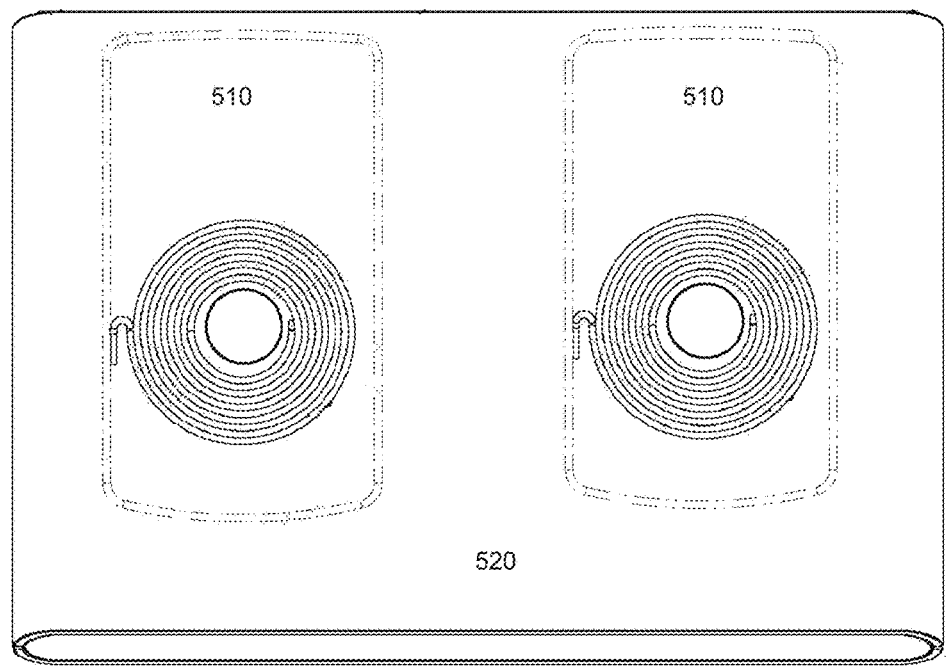
FIG. 5d depicts a plurality of wireless transfer stations integrated into an object in accordance with an example.

FIG. 5c illustrates one exemplary embodiment of the wireless transfer station 510 integrated into an object 520. In one embodiment, the object 520 that the wireless transfer station 510 can be integrated into can be an electronic device, such as a medical device or a wireless energy battery pack. In one example, the wireless transfer station 510 can be integrated into a medical infusion pump and provide energy to the medical infusion pump. In another embodiment, the object 520 can be integrated into a medical cart (such as a work surface of the medical cart), a floor mat, a floor surface, a plate mounted to a wall, a wall surface, chair railing, a room railing, a ceiling tile, a ceiling surface, and so forth. FIG. 5d illustrates that a plurality of wireless transfer stations 510 can be integrated into an object 520. FIG. 5d is the same as FIG. 5c in all other aspects.

Figure 6:
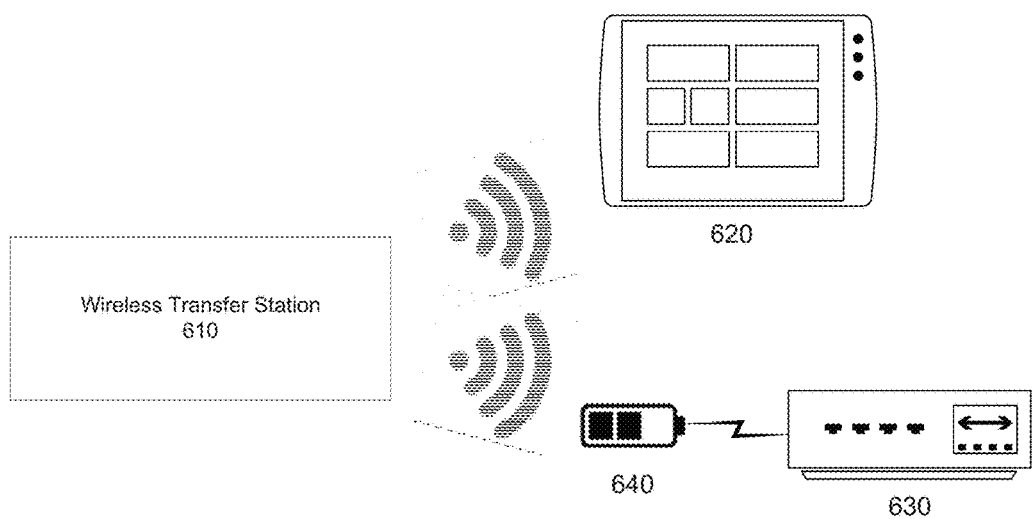
FIG. 6 depicts a wireless transfer station that can provide energy to one or more non-wire powered electronic devices and/or one or more recharge batteries coupled to a device in accordance with an example.

FIG. 6 shows a wireless transfer station 610 that can provide energy to one or more non-wire powered electronic devices 620 and/or one or more rechargeable batteries 640 coupled to a device 630. In another embodiment, the wireless transfer station 610 can provide energy to different types of non-wire powered electronic devices, such as a monitoring device, a computing device, a medical device, and so forth. In one example, the wireless transfer station 610 can provide a unified energy source for the devices 620 and 630 and/or the one or more rechargeable batteries 640 coupled to the device 630. In one embodiment, a unified energy source can be a power source that can provide power to a device, a wireless transfer station, and/or a battery without using different power connectors to provide the power to the device, the wireless transfer station, and/or the battery. In one embodiment, the wireless transfer stations can include an integrated wireless energy coil and a physical electrical energy connection terminal. In another embodiment, the wireless transfer station 610 can transfer energy via an electrical energy connection terminal and/or an integrated wireless transfer coil.

Figure 7A:
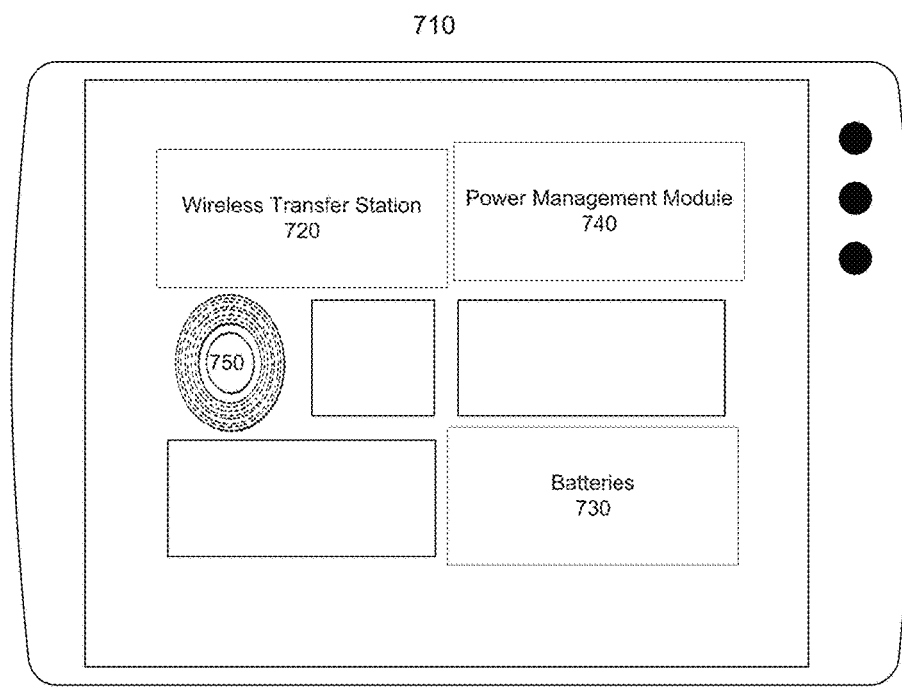
FIG. 7a depicts a device with a wireless transfer station coupled to a device or integrated into the device in accordance with an example.

FIG. 7a shows a device 710 with a wireless transfer station 720 coupled to the device 710 or integrated into the device 710. In one embodiment, the wireless transfer station 720 can be configured to provide energy to batteries 730 of the device 710 and the batteries 730 can provide energy to the device 710. In another embodiment, the wireless transfer station 720 can be configured to provide energy directly to the device 710, e.g. without using batteries. In one example, a power management module 740 can provide energy directly to the device 710 by receiving energy at a wireless transfer coil 750 of the wireless transfer station 710 from a wireless transfer coil of another wireless transfer station and direct the energy via the power management module 740 to the device 710 and/or the batteries 730.

Figure 7B:
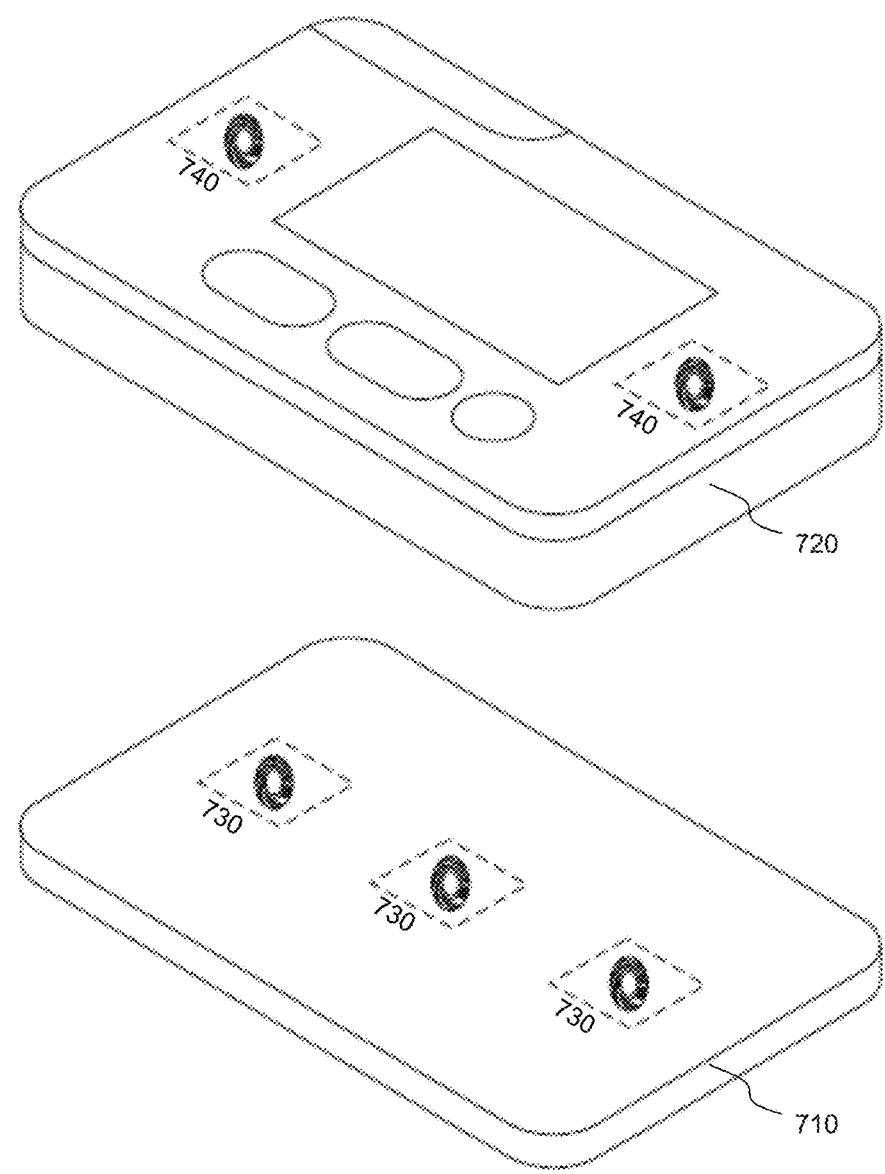
FIG. 7b depicts a wireless transfer station with a plurality of wireless transfer coils configured to transfer energy and/or data to an electronic device in accordance with an example.

FIG. 7b illustrates a wireless transfer station 710 with a plurality of wireless transfer coils 730 configured to transfer energy and/or data to an electronic device 720, such as a medical device. The medical device can include one or more integrated wireless transfer stations 740. In one embodiment, the electronic device 720 can be located adjacent to the wireless transfer station 710. For example, a bottom surface of the electronic device 720 can abut a top surface of the wireless transfer station 710.

In one embodiment, the wireless transfer station or one or more components of the wireless transfer station can be incorporated into a device. The device can be: a wheeled medical cart; a platform coupled the wheeled medical cart; a platform integrated into the wheeled medical cart; and/or a device coupled the wheeled medical cart.

FIGS. 8a, 8b, and 8c show a wheeled medical cart 810 with different configurations of integrated wireless transfer stations 820, 830, and 840, respectively. FIG. 8a shows a wheeled medical cart 810 with a plurality of wireless transfer stations 820 integrated into a selected area 852 of a work surface 850 of the wheeled medical cart 810. FIG. 8b shows a wheeled medical cart 810 with a plurality of wireless transfer stations 830 integrated into a work surface 860 of the wheeled medical cart 810. The wheeled medical cart 810 of FIG. 8b is the same as the wheeled medical cart 810 in FIG. 8a in all other regards. FIG. 8c shows a wheeled medical cart 810 with one or more of wireless transfer stations 840 integrated into a device holder 870 of the wheeled medical cart 810. The wheeled medical cart 810 of FIG. 8c is the same as the wheeled medical carts 810 in FIGS. 8a and 8b in all other regards.

In one embodiment, the wheeled medical cart 810 can have one or more attached work surfaces 850 or 860. In one example, the one or more work surfaces 850 or 860 and/or device holder 870 of the wheeled medical cart can include one or more integrated or coupled wireless transfer coils, such as one or more transmitting coils, one or more repeater coils, and/or one or more receiving coils. In another embodiment, the one or more work surfaces 850 or 860 and/or device holder 870 can have one or more selected areas for other devices, such as medical devices and/or mobile devices, to be placed on the one or more work surfaces 850 or 860 and/or device holder 870 and receive wireless energy.

In one embodiment, the device holder 870 can be designed to hold one or more devices at selected alignments to orient the one or more devices to receive energy from one or more of wireless transfer stations 840. In one example, the device holder 870 can be integrated into the wheeled medical cart 810 and the device holder 870 can hold and orient one or more medical devices to receive wireless energy using wireless transfer stations coupled to the medical devices and/or wireless transfer stations integrated into the medical devices.

In one embodiment, the wheeled medical cart 810 can include one or more electrical systems and/or one or more devices coupled to the wheeled medical cart 810. In another embodiment, the wheeled medical cart 810 can use one or more wireless transfer stations 880 to power the one or more electrical systems and/or the one or more devices. In another embodiment, the one or more wireless transfer stations 880 can receive wireless energy while attached to the wheeled medical cart. In another embodiment, the one or more wireless transfer stations 880 can be removed from the wheeled medical cart and can be attached to another wireless transfer station or be located adjacent to the wireless transfer station and receive wireless energy.

Figure 9:
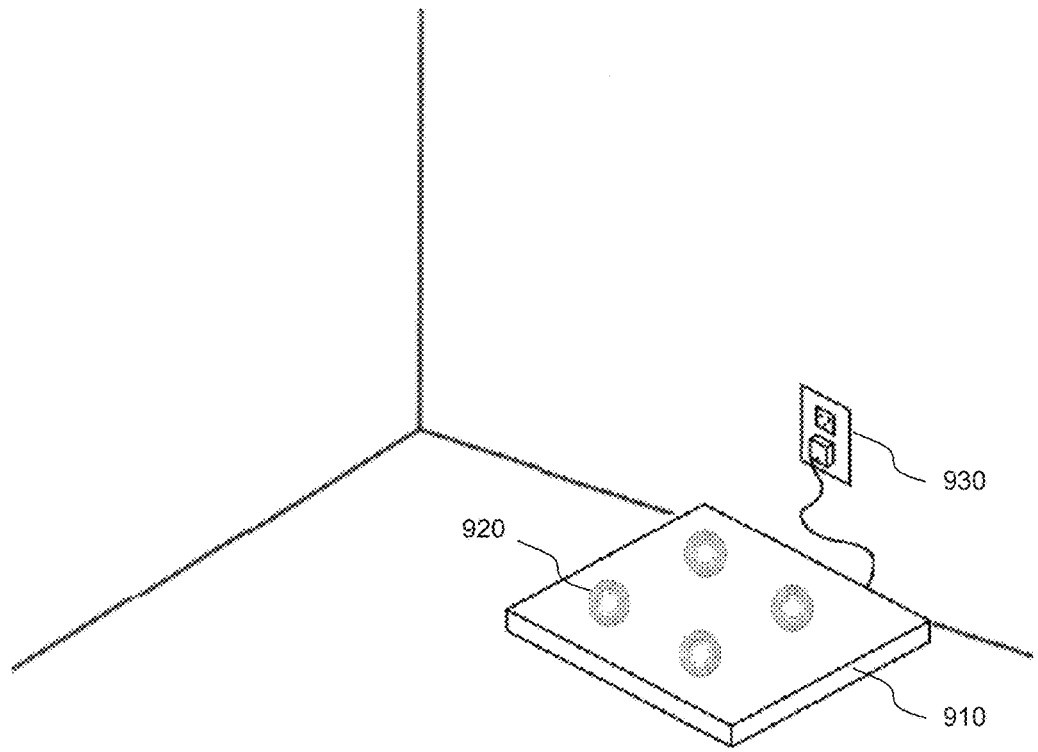
FIG. 9 depicts a floor mat with one or more integrated wireless transfer stations in accordance with an example.

FIG. 9 shows one exemplary embodiment of floor mat 910 with one or more integrated wireless transfer stations 920. In one embodiment, the integrated wireless transfer stations 920 can receive energy and/or data from an outlet 930. In one embodiment, the outlet 930 can be a wall outlet and the integrated wireless transfer stations 920 can receive alternating current (AC) from the outlet 930. In another embodiment, the outlet 930 can be a data outlet, such as an Ethernet outlet, and the integrated wireless transfer stations 920 can receive data from the outlet 930.

In another embodiment, the one or more integrated wireless transfer stations 920 can include one or more wireless transfer coils to transfer energy from the wireless transfer station 920 to another wireless transfer station. In one example, a wireless transfer station coupled to a wheeled medical cart can be moved into a location in proximity or adjacent to the wireless transfer station integrated 920 into the floor mat 910 and receive energy from the one or more wireless transfer stations 920 integrated into the floor mat 910.

Figure 10:
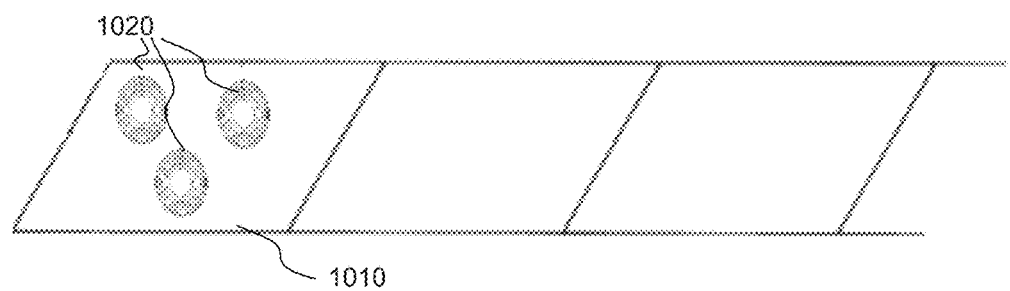
FIG. 10 depicts a flooring surface with one or more integrated wireless transfer stations in accordance with an example.

FIG. 10 shows one exemplary embodiment of a flooring surface 1010 with one or more integrated wireless transfer stations 1020. In another embodiment, the one or more integrated wireless transfer stations 1020 can include one or more wireless transfer coils. In another embodiment, the flooring surface 1010 can be a flooring tile with the one or more integrated wireless transfer stations 1020 integrated into the flooring tile. In another embodiment, the one or more integrated wireless transfer stations 1020 can be coupled to the flooring surface, such as attached to an outer surface of a flooring tile.

Figure 11:
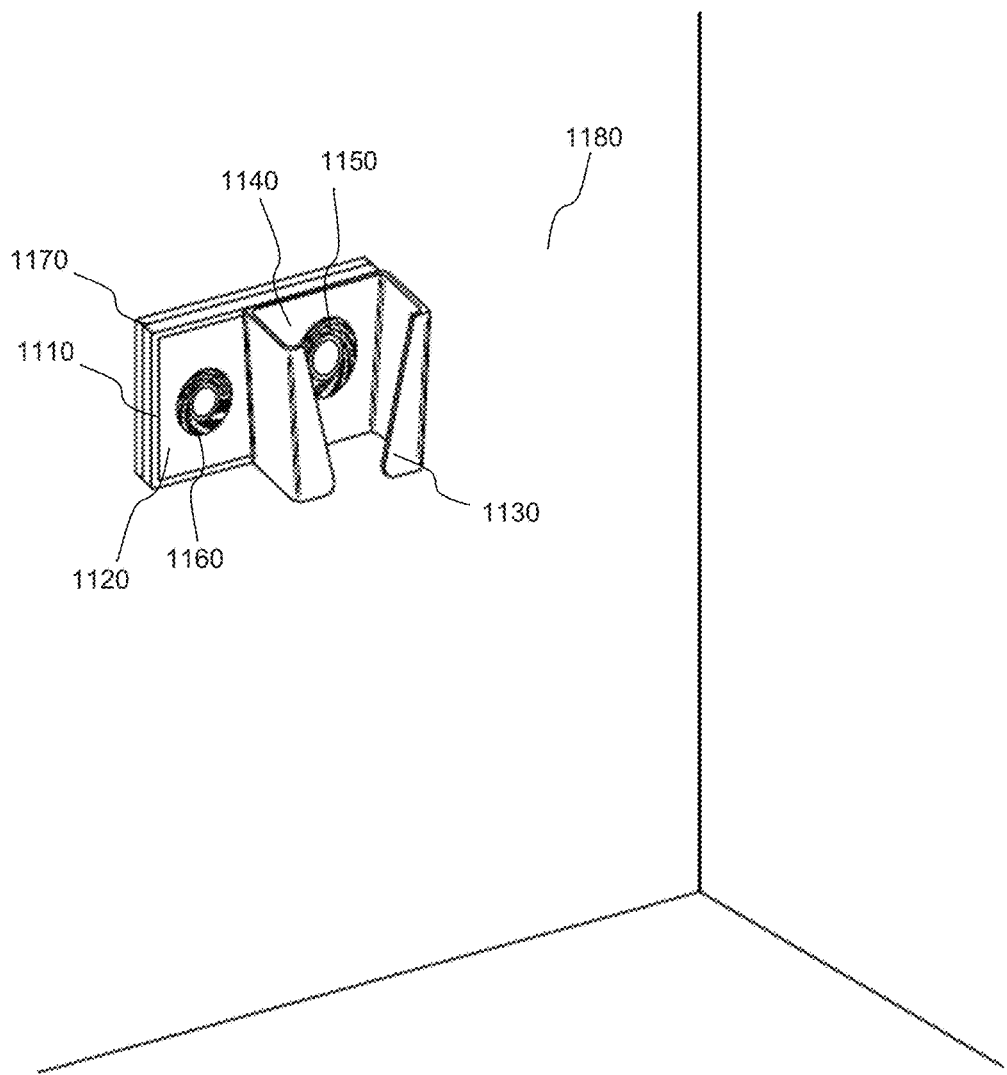
FIG. 11 depicts a plate mounted to a wall with one or more integrated wireless transfer stations in accordance with an example.

FIG. 11 shows one exemplary embodiment of a plate 1110 mounted to a wall 1180 with one or more integrated wireless transfer stations 1120. In another embodiment, the one or more integrated wireless transfer stations 1120 can include one or more wireless transfer coils 1160. In another embodiment, the plate 1110 can be integrated into the wall 1180. In another embodiment, the one or more integrated wireless transfer stations 1120 can be coupled to the wall 1180, such as attached to an inner surface of the wall 1180. In another embodiment, a receptacle 1130 can be attached to the plate 1110. In another embodiment, the receptacle 1130 can receive a device, such as a medical device, or another wireless transfer station. In another embodiment, one or more wireless transfer stations 1140 can be coupled to the receptacle 1130 and the one or more wireless transfer stations 1140 can be used to transfer energy and/or data with the device or the other wireless transfer station, such as by using a wireless transfer coil 1150.

In another embodiment, a plate 1110 can be attached to a mounting plate 1170 that is attached to the wall 1180. One advantage of attaching the plate 1110 to the mounting plate 1190 can be that the plate 1110 can be easily and/or quickly removed from the mounting plate 1170 for maintenance, upgrades, replacement, and so forth. In one embodiment, the plate 1110 can be attached to the mounting plate 1170 using one or more fasteners or connectors, such as hooks, quick connectors, screws, bolts, and so forth.

In one embodiment, the wireless transfer station can monitor an amount of energy and/or data transmitted by a wireless transfer coil and/or an amount of energy and/or data received by the wireless transfer coil. In one example, a first wireless transfer station with a receiving coil can communicate energy information to a second wireless transfer station with a transmitting coil, using a communications module as discussed in the preceding paragraphs. The energy information can include: voltage level information, current draw level information, energy level information of the energy received at the receiving coil, energy level information of the energy transmitted from the transmitting coil, internal temperature information, ambient temperature information, or other types of desired metrics.

In one embodiment, the wireless transfer station can adjust an amount of energy transmitted from a wireless transfer coil of a wireless transfer station to another wireless transfer coil of another wireless transfer station based on the energy information. In one example, if a device with an integrated or coupled wireless transfer station requires 5 volts (V) and 2 amps (A) of energy and is currently receiving a voltage level or an amperage level at a level above or below a selected energy level range (such as a voltage range and/or a current range), the device or the coupled wireless transfer station can communicate the energy information to the wireless transfer station. In this example, the wireless transfer station can adjust the energy transferred from the wireless transfer coil to the other wireless transfer coil to bring the energy level range received at a wireless transfer coil to a level within a selected energy level range.

In another embodiment, a wireless transfer station can be a communication hub between multiple devices and/or other wireless transfer stations. In one example, the wireless transfer station can be integrated into a medical cart. The medical cart can receive data from a first device using a communication module (as discussed in the preceding paragraphs) and relay the data to another wireless transfer station, such as a wireless transfer station attached to a wall or floor.

In one embodiment, the wireless transfer station can regulate an amount of energy received by one or more other wireless transfer stations. In one example, when a first wireless transfer station uses a wireless transfer coil to transfer energy, the first wireless transfer station can control the amount of energy received at a second wireless transfer station by detuning a frequency of the wireless transfer coil of the first wireless transfer station by a selected amount. In another example, the first wireless transfer station can control the amount of energy received from the second wireless transfer station by detuning a frequency of the wireless transfer coil of the first wireless transfer station by selected amount.

Figure 12:
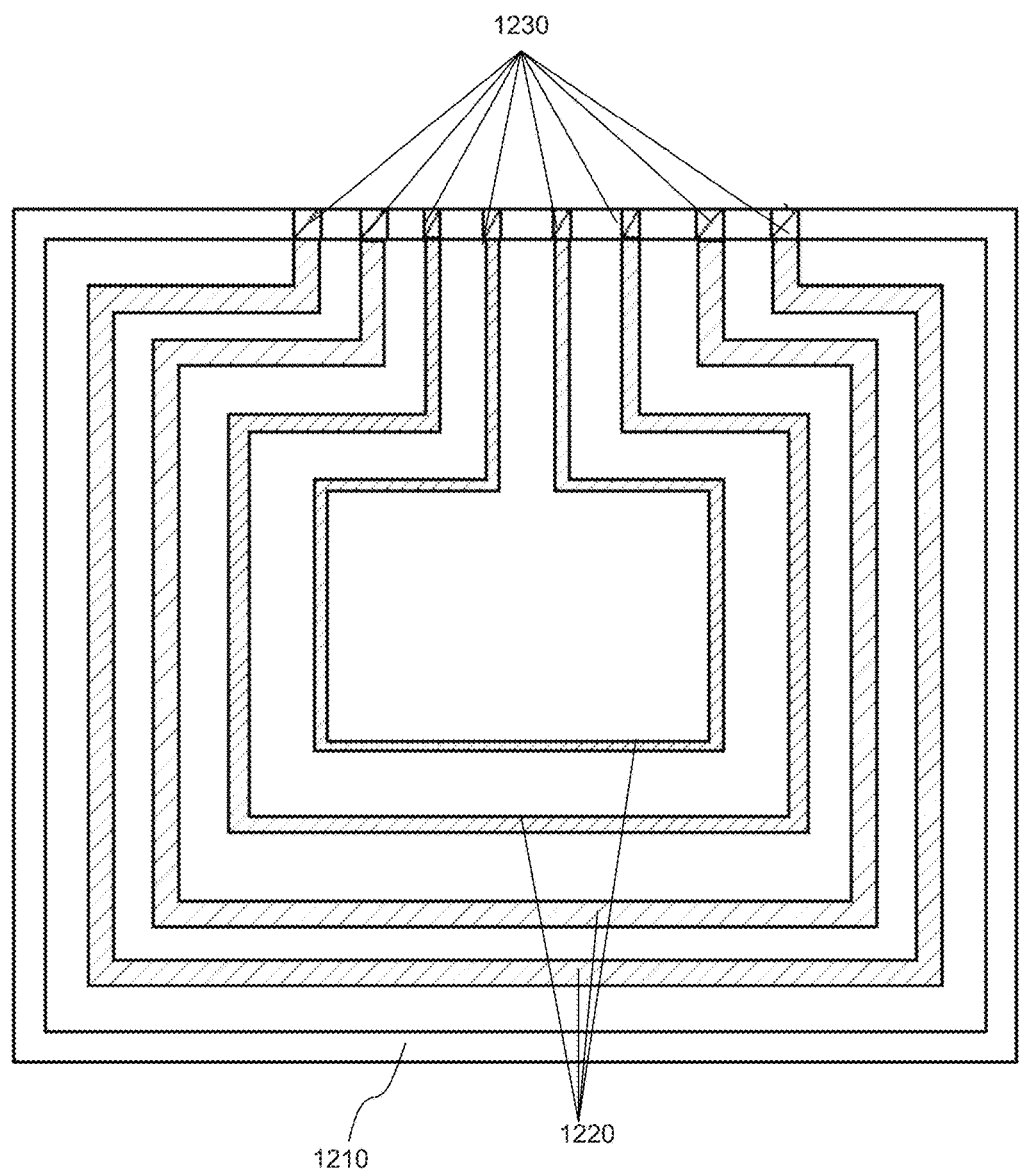
FIG. 12 depicts a wireless transfer coil with a plurality of loops or winds in accordance with an example.

FIG. 12 shows a wireless transfer coil 1210 with a plurality of loops or winds 1220. In one embodiment, an amount of energy transmitted and/or received by the wireless transfer coil 1210 can be adjusted using one or more adjustment modules 1230. In one embodiment, the one or more adjustment modules 1230 can engage or disengage one or more of the plurality of loops 1220 to: effectively vary a size of the wireless transfer coil 1210; change a number of active loops of the wireless transfer coil 1210; change a shape of a magnetic field of the wireless transfer coil 1210; change an amount of energy transferred using the wireless transfer coil 1210; or enable or disable selected devices from receiving energy and/or data from the wireless transfer coil 1210.

In one embodiment, the one or more adjustment modules 1230 can be one or more switches, such as an impedance matching switch or an on/off switch. In one example, a selected number of the plurality of loops 1220 can be engaged by turning on one or more of the corresponding switches and a selected number of the plurality of loops 1220 can be disengaged by turning off one or more of the corresponding switches.

In one embodiment, a resonant frequency between of the wireless transfer coil 1210 can be dynamically adjusted using the one or more adjustment modules 1230. In one embodiment, the one or more adjustment modules 1230 can be adjustable energy oscillators. In another embodiment, the one or more adjustment modules 1230 can be variable capacitors, variable inductors, and/or variable inductors and the respective capacitance, resistance, and/or inductance can be changed to tune or detune the wireless transfer coil 1210.

In one embodiment, a wireless transfer coil of a first wireless transfer station can have a fixed impedance and/or resonant frequency and an impedance and/or resonant frequency of a second wireless transfer coil of a second wireless transfer station can be adjustable. In another embodiment, the impedance and/or resonant frequency of the wireless transfer coil of the first wireless transfer station and the impedance and/or resonant frequency of the wireless transfer coil of the second wireless transfer station can each be adjustable.

In one embodiment, the wireless transfer station can be a wheeled medical cart. In another embodiment, the wheeled medical cart can include one or more receiving coils attached to a support column of the wheeled medical cart and/or integrated into the support column of the wheeled medical cart to receive wireless energy from another wireless transfer station. In another embodiment, the support column of the wheeled medical cart can include an electrical connector and/or energy cables to receive energy from a battery and/or an energy source.

Figure 13:
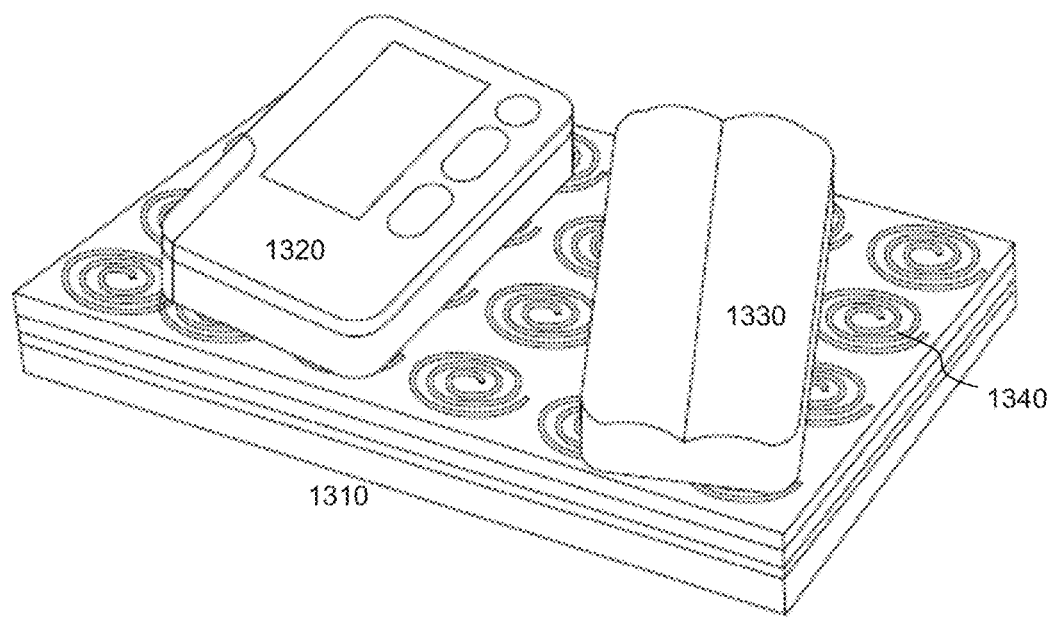
FIG. 13 depicts a wireless transfer hub transferring energy and/or information with an electronic device and/or another wireless transfer station using wireless transfer coils in accordance with an example.

In one embodiment, a wireless transfer station can be a wireless transfer hub (e.g. energy and/or data transfer) for a plurality of selected devices and/or other wireless transfer stations. FIG. 13 illustrates a wireless transfer hub 1310 transferring energy and/or information with an electronic device 1320, such as a medical device, and/or another wireless transfer station 1330 using wireless transfer coils 1340. In one embodiment, the electronic device 1320 and the other wireless transfer station 1330 can exchange energy and/or information with the wireless transfer station 1310 at the same time or at different times. In another embodiment, the electronic device 1320 and the other wireless transfer station 1330 can transfer energy and/or information with the wireless transfer hub 1310 using different wireless transfer coils 1340.

In one example, the wireless transfer hub 1310 coupled to a medical cart can wirelessly provide selected levels of energy to systems and subsystems of the medical cart and/or other devices coupled to the medical cart. In one embodiment, the wireless transfer hub 1310 coupled to the medical cart can receive energy and/or data from a wireless transfer station and relay the energy and/or data to systems and subsystems of the medical cart and/or other devices using one or more repeater coils.

In one embodiment, a medical cart or a device can have an integrated wireless transfer station to provide energy to systems and/or subsystems of the medical cart or the device when one or more external wireless transfer stations (e.g. non-integrated wireless transfer stations) are being recharged. In one embodiment, the integrated wireless transfer station can include one or more wireless transfer coils to receive energy and/or data from another wireless transfer station. In one example, the medical cart or the device can receive energy from the one or more external wireless transfer stations until an energy level of the one or more external wireless transfer stations is depleted or decreases below a threshold energy level. In this example, when the energy level of the one or more external wireless transfer stations is depleted or decreases below a threshold energy level, the medical cart or the device can be positioned adjacent a transmitter coil of another wireless transfer station and the one or more external wireless transfer stations can receive energy for recharging. In one embodiment, while the one or more external wireless transfer stations receive energy for recharging, the integrated wireless transfer station can provide energy to the medical cart or the device.

In one embodiment, the integrated wireless transfer station can receive energy from the other wireless transfer station to recharge one or more batteries of the integrated wireless transfer station. In another embodiment, the integrated wireless transfer station can receive energy from the one or more external wireless transfer stations to recharge the one or more batteries of the integrated wireless transfer station. In another embodiment, when the one or more external wireless transfer stations receive energy from another wireless transfer station, the one or more external wireless transfer stations can provide partial or full energy to the medical cart or the device.

In one embodiment, when the energy level of the one or more external wireless transfer stations is depleted or decreases below a threshold energy level, the one or more external wireless transfer stations can be removed from the medical cart or the device and placed adjacent a transmitter coil of another wireless transfer station to receive energy to recharge the external wireless transfer station. In one embodiment, while the one or more external wireless transfer stations are removed for recharging and/or until one or more other external wireless transfer stations are attached to the medical cart or the device, the integrated wireless transfer station can provide energy to one or more system or subsystem of the medical cart or the device. In one embodiment, when the medical cart or the device is placed adjacent to a transmitter coil of a wireless transfer station, the integrated wireless transfer station can receive energy from the wireless transfer station to recharge the integrated wireless transfer station.

In one embodiment, the medical cart or a device can include a wireless transfer coil to transfer energy and/or data with another wireless transfer station. In one example, the medical cart or a device can use the wireless transfer coil to receive energy and provide energy directly to one or more systems and/or subsystems of the medical cart or the device and/or provide energy to an energy source, such as a battery, of the medical cart or the device. In one example, the medical cart or the device with the wireless transfer coil can be placed near a transmitter coil of a wireless transfer station and the wireless transfer coil can relay energy to one or more systems and/or subsystems of the medical cart or the device.

Figure 14:
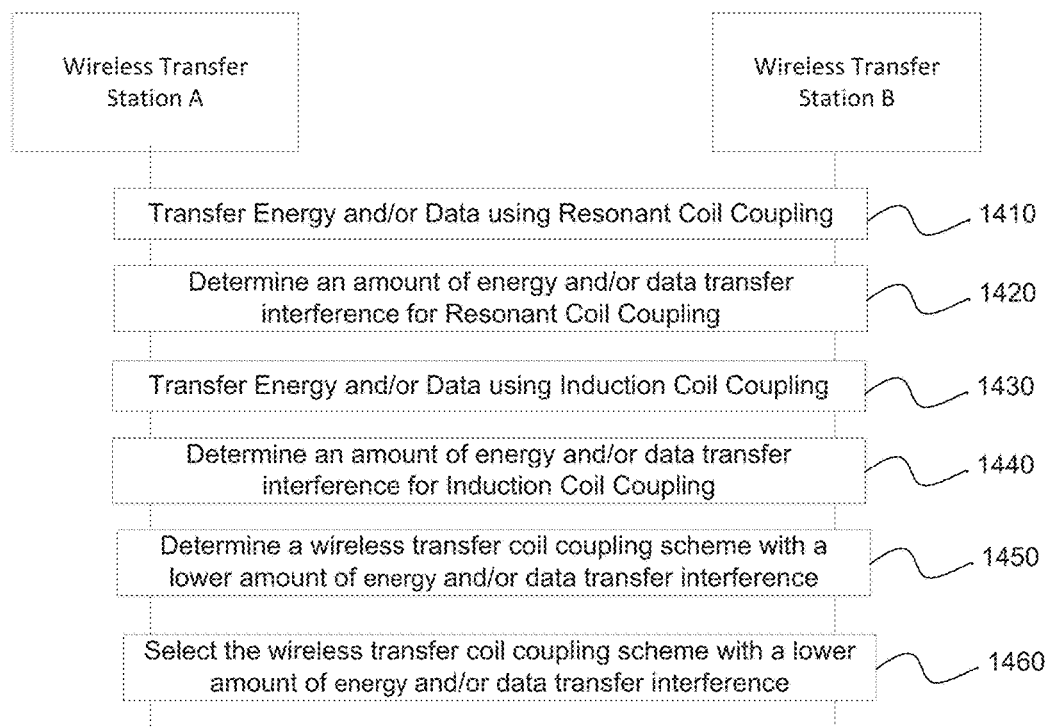
FIG. 14 shows a framework for a wireless transfer station and another wireless transfer station selecting a resonant wireless transfer coil pair or an induction wireless transfer coil pair for transferring energy and/or data in accordance with an example.

FIG. 14 shows a wireless transfer station A and a wireless transfer station B selecting a resonant wireless transfer coil pair or an induction wireless transfer coil pair for transferring energy and/or data. In one embodiment, the wireless transfer station A can transfer energy and/or data with the wireless transfer station B using a resonant wireless transfer coil pair, as in block 1410. In another embodiment, the wireless transfer station A and/or the wireless transfer station B can determine an amount of energy and/or data transfer interference between a wireless transfer coil of the wireless transfer station A and a wireless transfer coil of the wireless transfer station A for resonant wireless transfer coil coupling, as in block 1420.

In one embodiment, the wireless transfer station A can transfer energy and/or data with the wireless transfer station B using an induction wireless transfer coil pair, as in block 1430. In another embodiment, the wireless transfer station A and/or the wireless transfer station B can determine an amount of energy and/or data transfer interference between a wireless transfer coil of the wireless transfer station A and a wireless transfer coil of the wireless transfer station A for induction wireless transfer coil coupling, as in block 1440. In one embodiment, the energy and/or data transfer interference can be an amount of noise between the wireless transfer coil pair while energy and/or data is transferred between a wireless transfer coil pair. In another embodiment, the wireless transfer station A and/or the wireless transfer station B can compare the amount of energy and/or data transfer interference for resonant wireless transfer coil coupling and induction wireless transfer coil coupling to determine a wireless transfer coil coupling scheme with a lower amount of energy and/or data transfer interference, as in block 1450. In another embodiment, the wireless transfer station A and/or the wireless transfer station B can select the wireless transfer coil coupling scheme with a lower amount of energy and/or data transfer interference, as in block 1460.

Figure 15:
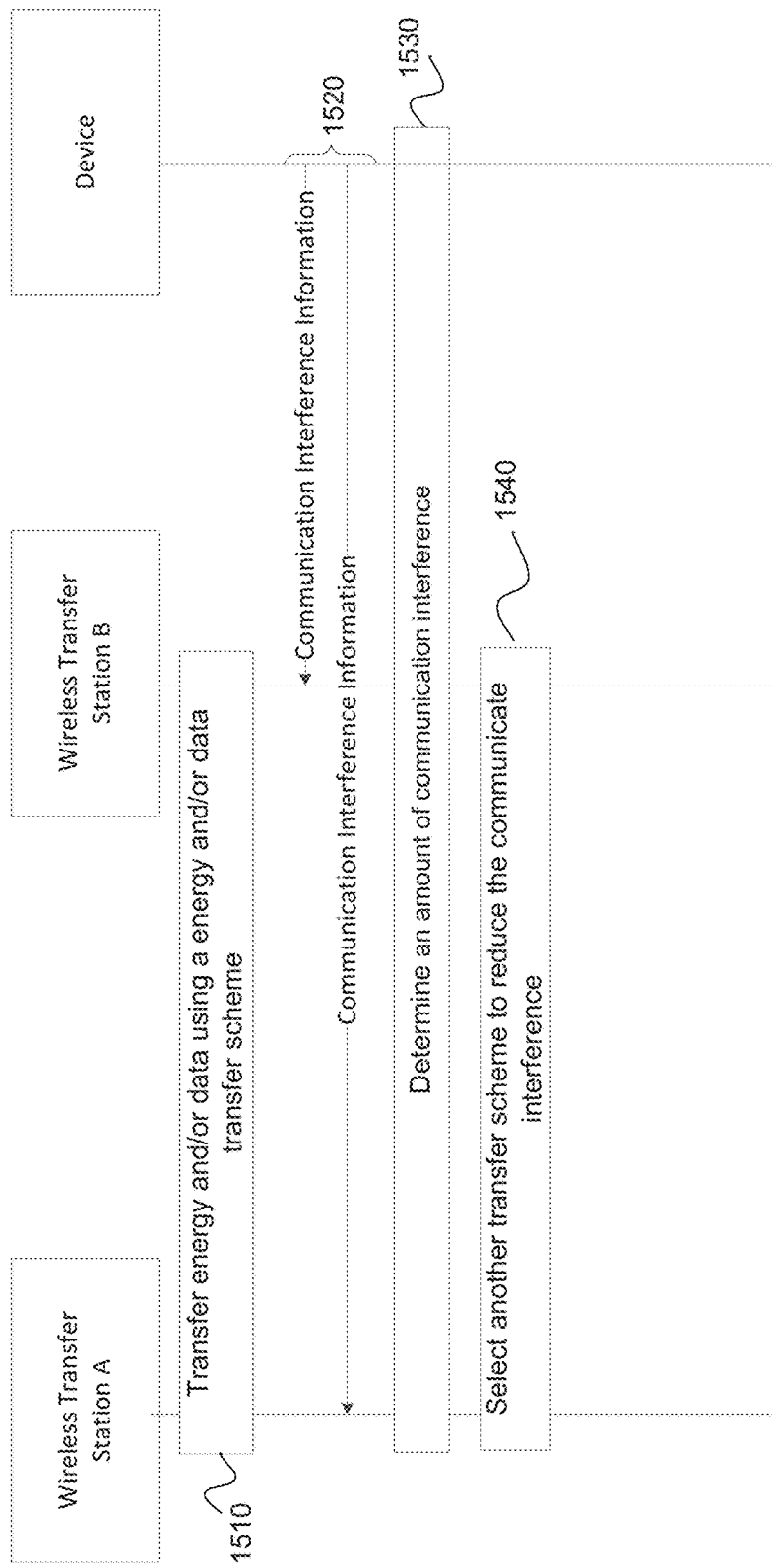
FIG. 15 shows a framework for a wireless transfer station, another wireless transfer station, and a device to select a transfer scheme to reduce a communication interference from the energy and/or data transfer between the wireless transfer station and the other wireless transfer station in accordance with an example.

In another embodiment, a transfer of energy between a wireless transfer coil pair may cause communication interference for communications by other devices within the range of the wireless transfer coil pair. FIG. 15 shows a wireless transfer station A, a wireless transfer station B, and a device selecting a transfer scheme to reduce a communication interference from the energy and/or data transfer between the wireless transfer station A and the wireless transfer station B. In one embodiment, the wireless transfer station A and the wireless transfer station B can transfer energy and/or data using an energy and/or data transfer scheme (such as magnetic induction coupling or magnetic resonance coupling), as in block 1510. In another embodiment, the devices can communicate interference information to wireless transfer station A and/or the wireless transfer station B, as in block 1520. In one embodiment, the communication interference information can include an interference level of a communication between the device and another device. In another embodiment, the wireless transfer station A, the wireless transfer station B, and/or the device can determine an amount of communication interference to the communications of the device, as in block 1530. In another embodiment, when the amount of communication interference exceeds a selected threshold limit, the wireless transfer station A and the wireless transfer station B can select another transfer scheme to reduce the communicate interference, as in block 1540.

In one embodiment, the transfer scheme can include using magnetic resonant coupling and the other transfer scheme can include using magnetic induction coupling, or vice versa. In another embodiment, the transfer scheme can include magnetic resonant coupling or magnetic induction coupling and the other transfer scheme can include ceasing to transfer energy and/or data between the wireless transfer station A and the wireless transfer station B for a selected period of time, such as a period of time when the device is communicating with the other device. In another embodiment, the wireless transfer station A and the wireless transfer station B can determine a communication interference level for an energy and/or data transfer using magnetic induction and a communication interference level for an energy and/or data transfer using magnetic resonance and select the transfer scheme with a lower communication interference level.

Figure 16:
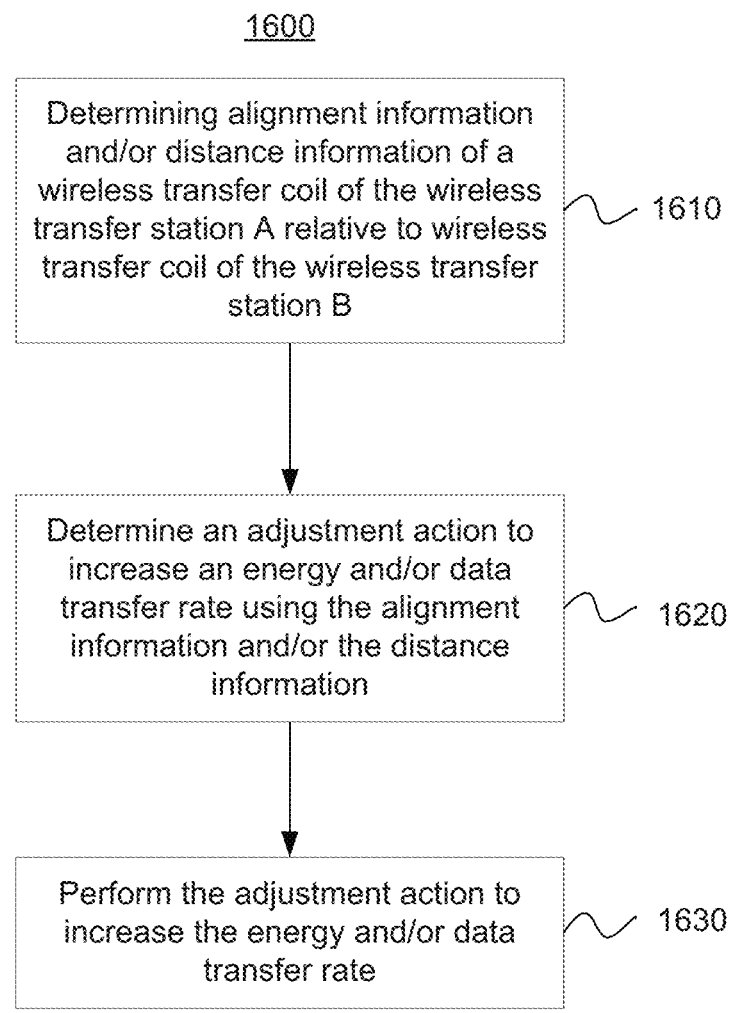
FIG. 16 illustrates a method for adjusting an alignment and/or distance of a wireless transfer coil of a wireless transfer station relative to a wireless transfer coil of another wireless transfer station in accordance with an example.

FIG. 16 shows a flowchart 1600 of a method for adjusting an alignment and/or distance of a wireless transfer coil of the wireless transfer station A relative to a wireless transfer coil of the wireless transfer station B. In one embodiment, the method can comprise of determining alignment information and/or distance information of a wireless transfer coil of the wireless transfer station A relative to wireless transfer coil of the wireless transfer station B, as shown in block 1610. In one embodiment, the wireless transfer station A and/or the second wireless transfer station B can determine the alignment of the wireless transfer coils and/or the distance between the wireless transfer coils using triangulation. In one example, the wireless transfer station A can include a plurality of transmitting coils and the wireless transfer station B can measure an amount of energy received from two or more of the plurality of transmitting coils at one or more receiving coils of the wireless transfer station B to triangulate the alignment of the wireless transfer coils and/or the distance between the wireless transfer coils. In another embodiment, the wireless transfer station B can determine the alignment of the wireless transfer coils and/or the distance between the wireless transfer coils by measuring an increase or decrease in an amount of energy received at the receiving coil of the wireless transfer station B from the transmitting coil of wireless transfer station A as the receiving coil and/or the transmitting coil is moved to different locations.

In another embodiment, the wireless transfer station A and/or the wireless transfer station B can determine an adjustment action to increase an energy and/or data transfer rate using the alignment information and/or the distance information, as shown in block 1620. In one embodiment, the adjustment action can be: changing a location of the wireless transfer coil of the wireless transfer station A and/or the wireless transfer station B; adjusting a transmitting power level of the transmitting coil; changing an orientation of the wireless transfer coil of the wireless transfer station A and/or the wireless transfer station B; changing a wireless transfer coil coupling frequency; and so forth.

In one embodiment, the wireless transfer station A and/or the wireless transfer station B can perform the adjustment action to increase the energy and/or data transfer rate between the wireless transfer station A and the wireless transfer station B, as shown in block 1630. In another embodiment, the wireless transfer station A and/or the wireless transfer station B can indicate to a user of the wireless transfer station A and/or the wireless transfer station B the adjustment action. In another embodiment, the wireless transfer station A and/or the wireless transfer station B can include an adjustment mechanism, such as an actuator or motor, to move a wireless transfer coil.

In wireless energy and/or data transfer, foreign objects (such as metal objects or other electrically conductive objects) that are adjacent to a wireless transfer coil of a wireless transfer station can couple to a portion of a magnetic field, such as an electromagnetic field, of the wireless transfer coil. In one embodiment, a foreign object can be any object that intrudes into a magnetic coupling field between a first wireless transfer coil and a second wireless transfer coil. In one example, the foreign object can be: a cord, such as an electrical cord; keys; a biological object, such as a human hand; a metal plate or disc; and so forth. In another example, a foreign object can include biological and/or non-biological material.

In one embodiment, when a foreign object with conductive material couples with the magnetic field, the foreign object may heat up. In another embodiment, the foreign object can also interfere with a magnetic field emitted from the wireless transfer coil of the wireless transfer station. In one example, a coupling of the foreign object with the magnetic field of the wireless transfer coil and/or interference caused by the foreign object can result in: an energy wastage; safety issues; an inefficient transfer of energy; an incomplete data transfer; decreased energy and/or data transfer rates; and so forth. In another example, when the foreign object is in the vicinity or adjacent to a coupling link between a transmitting coil and a receiving coil, the transmitting coil and/or the receiving coil can experience a change of frequencies and/or impedances because of the adjacent foreign object.

In one embodiment, a wireless transfer station can determine a location of a foreign object by comparing an expected amount of energy or data transferred with another wireless transfer station with an actual amount of energy or data transferred with another wireless transfer station. In another embodiment, the wireless transfer station can determine a location of a foreign object by monitoring an increase or decrease in an amount of energy and/or data transferred or an increase or decrease in a rate that the energy and/or data is transferred as a wireless transfer coil of the wireless transfer station is moved to different locations relative to the foreign object.

In one embodiment, variations in an alignment of a first wireless transfer coil relative to a second wireless transfer coil and/or a distance between the first wireless transfer coil and the second wireless transfer coil can increase or decrease an efficiency of a coupling between the first wireless transfer coil and the second wireless transfer coil. In one example, the increase or decrease in efficiency in coupling can affect an accuracy of a wireless transfer station detecting a foreign object. In one embodiment a first wireless transfer station with a first wireless transfer coil and a second wireless transfer station with a second wireless transfer coil can communicate alignment and/or distance information of the first wireless transfer coil and the second wireless transfer station to determine an alignment of the first wireless transfer coil relative to the second wireless transfer coil and/or the distance between the first wireless transfer coil and the second wireless transfer coil.

In one embodiment, the first wireless transfer station and/or the second wireless transfer station can filter out an effect of the alignment of the first wireless transfer coil relative to the second wireless transfer station and/or an effect of the distance between the first wireless transfer coil and the second wireless transfer coil when determining the presence of a foreign object in a magnetic field of the transmitting coil. In another embodiment, the first wireless transfer station and/or the second wireless transfer station can monitor an energy draw, e.g. a current draw and/or a voltage draw, between the first wireless transfer coil and the second wireless transfer coil. In one example, the first wireless transfer station and/or the second wireless transfer station can detect variations or imbalances in the energy draw and determine that a foreign object is interfering with a wireless energy and/or data transfer. One advantage of a wireless transfer station detecting the presence of a foreign object in a magnetic field of a wireless transfer coil is to prevent energy wastage and minimize safety issues.

In one embodiment, an amount of energy and/or data transferred by a wireless transfer station can be adjusted based on a proximity of a biological entity (such as a human) to the wireless transfer station. In one example, an amount of energy transferred by the wireless transfer station can be decreased when a human is within a selected distance of the wireless transfer station.

In another embodiment, a wireless transfer coil of a wireless transfer station can be shielded from interfering foreign objects. In one embodiment, a Ferrite object (such as a Ferrite plate) can be located adjacent the wireless transfer coil and used to limit a magnetic field within a selected area. In another embodiment, the Ferrite object can be located adjacent to the wireless transfer coil of the wireless transfer station to shield the wireless transfer coil from the foreign object. In one example, a wireless transfer coil can be integrated into a wall or floor of a building or can be located adjacent to a wall or floor. In this example, the wall or floor can contain foreign objects, such as electrically conductive metal support beams. In one embodiment, the Ferrite object can be placed between the wireless transfer coil and the foreign object to shield the magnetic field of the wireless transfer coil from interference caused by the foreign object. In another embodiment, the Ferrite object can be placed between the wireless transfer coil and the foreign objects to redirect the magnetic field of the wireless transfer coil to avoid interference from the foreign objects. In another embodiment, the Ferrite object can be used to direct the magnetic field to radiate away from the foreign object. In another embodiment, a thin conductive plate can be placed behind a Ferrite plate to suppress interference and provide additional shielding to the magnetic field of the wireless transfer coil.

Figure 17:
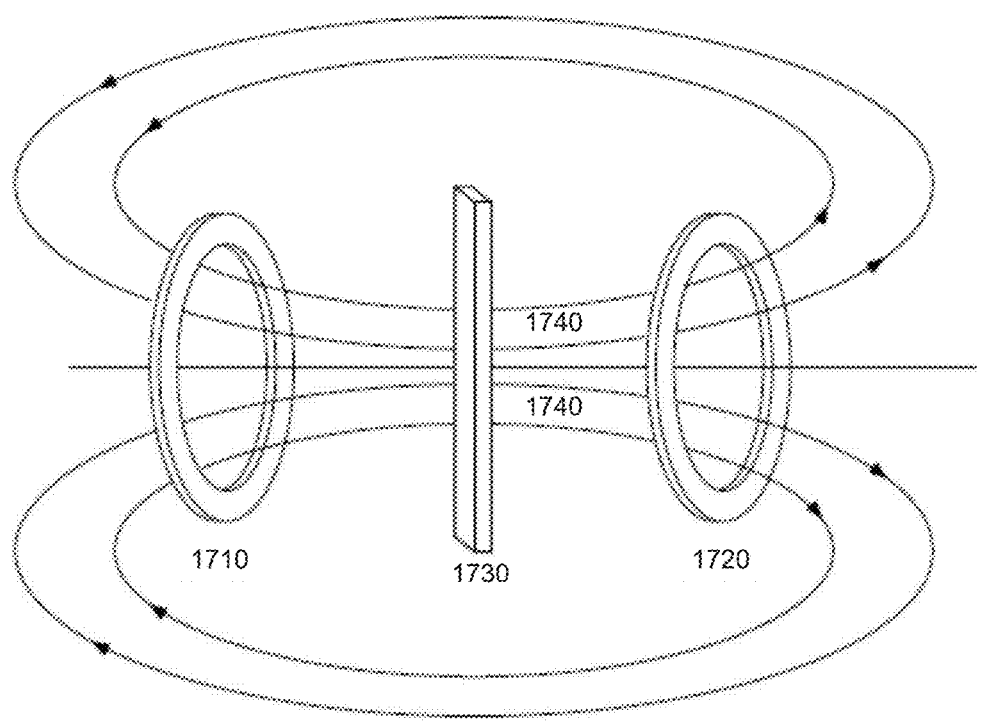
FIG. 17 depicts a foreign object entering a magnetic field between wireless transfer coils in accordance with an example.
Figure 18:
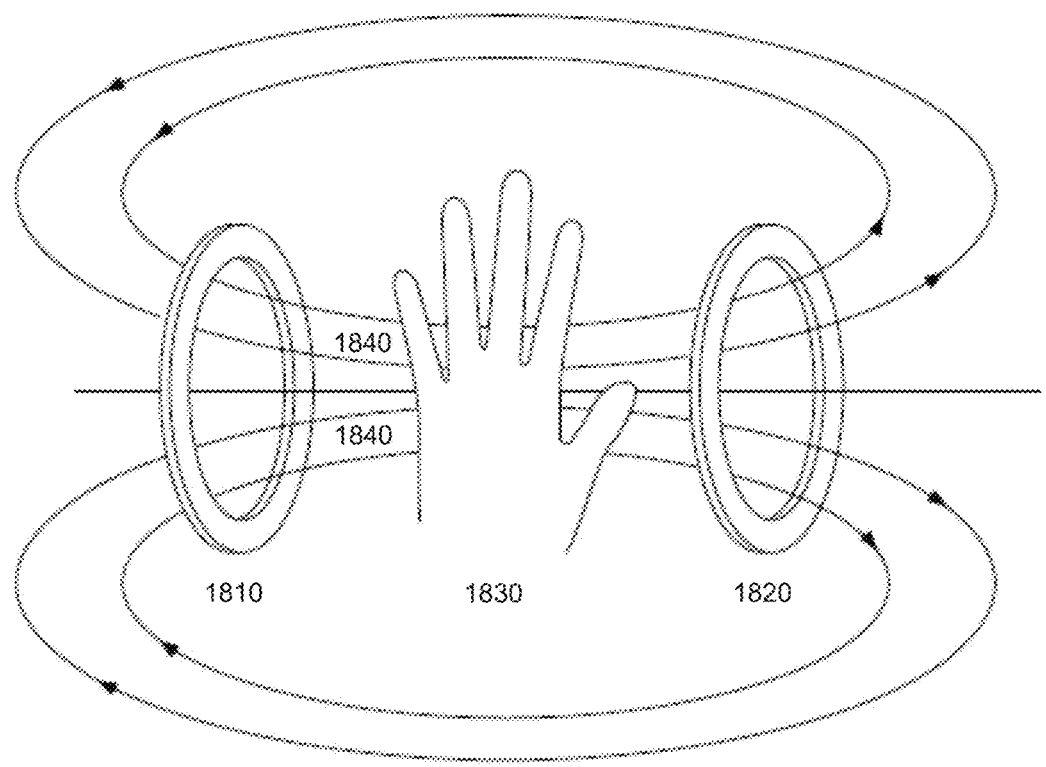
FIG. 18 depicts another foreign object entering a magnetic field between wireless transfer coils in accordance with an example.

FIG. 17 illustrates a foreign object 1730 entering a magnetic field 1740 between wireless transfer coil 1710 and wireless transfer coil 1720. In one embodiment, the foreign object 1730 is an electrically conductive foreign object, such as a metal plate or electrical cord. FIG. 18 illustrates a foreign object 1830 entering a magnetic field 1840 between wireless transfer coil 1810 and wireless transfer coil 1820. In one embodiment, the foreign object 1830 is a biological object, such as a human hand or human body part. In FIGS. 17 and 18, foreign objects 1730 and 1830 can interfere with the magnetic field 1740 or 1840, respectively. In one example foreign objects 1730 and 1830 can absorb the magnetic field 1740 or 1840, respectively.

In one embodiment, the wireless transfer station can be at a location that does not have any foreign objects that interfere with a wireless energy and/or data transfer. In one example, a first wireless transfer station and/or a second wireless transfer station can compare energy and/or data transferred to a wireless transfer coil of a second wireless transfer station with energy and/or data transferred from a wireless transfer coil of the first wireless transfer station. In another embodiment, the wireless transfer station can determine an amount of energy and/or data lost during an energy and/or data transfer between the first wireless transfer station and the second wireless transfer station without any interference from a foreign object using the compared energy and/or data transfer.

In one example, a wireless transfer coil of a first wireless transfer station can be a transmitting coil and the first wireless transfer station can determine an amount of energy being transmitted by the transmitting coil. The first wireless transfer station can communicate the transmitted energy information to a second wireless transfer station with a receiving coil. The second wireless transfer station can receive the transmitted energy information from the first wireless transfer station and compare the amount of transmitted energy with an amount of energy received at the second wireless transfer station. In one embodiment, when an amount of energy loss exceeds a threshold energy loss amount, the second wireless transfer station can determine that a foreign object is within the magnetic field of the wireless transfer coils.

In one embodiment, the first wireless transfer station and/or the second wireless transfer station can determine an energy or data loss value. In another embodiment, the energy or data loss value can be a difference between an amount of transmitted energy or data from the first wireless transfer station and an amount of energy or data received at the second wireless transfer station. In another embodiment, the first wireless transfer station and/or the second wireless transfer station can determine that a foreign object is within the electromagnetic field when the energy loss value exceeds a selected threshold. In another embodiment, when energy loss value exceeds the selected threshold or exceeds the selected threshold by a selected amount, the first wireless transfer station can stop transferring energy.

In one embodiment, when a wireless transfer station with a wireless transfer coil detects a foreign object in a magnetic field of the wireless transfer coil, the wireless transfer station can change the amount of energy and/or data transferred by the wireless transfer coil (such as turning off the wireless transfer coil or decreasing an amount of energy and/or data transferred). In another embodiment, when the wireless transfer station includes a wireless transfer coil array, the wireless transfer station can switch from transferring energy and/or data from one wireless transfer coil to transferring energy and/or data from another wireless transfer coil of the wireless transfer coil array.

In one embodiment, a wireless transfer station can change a frequency of a wireless transfer coil from a frequency at which a foreign object resonates to a frequency at which the foreign object does not resonate. In one example, when the wireless transfer station detects a foreign object interfering with a wireless energy transfer, the wireless transfer station can determine a different frequency that can minimize or eliminate the interference caused by the foreign object. In this example, when the wireless transfer station determines the different frequency, the wireless transfer station and another wireless transfer station can switch energy and/or data transfer frequencies to the different frequency for transferring wireless energy and/or data.

In one embodiment, a first wireless transfer station can communicate with a second wireless transfer station to determine a frequency capability of the second wireless transfer station, or vice versa. In one example, when the first wireless transfer station determines the frequency capability of the second wireless transfer station, the first wireless transfer station can select a frequency for a wireless transfer coil of the first wireless transfer station to transfer energy and/or data to a wireless transfer coil of the second wireless transfer station. In this embodiment, the first wireless transfer station can communicate selected frequency information to the second wireless transfer station and transfer energy and/or data from the wireless transfer coil of the first wireless transfer station using the selected frequency.

In another example, when the second wireless transfer station determines the frequency capability of the first wireless transfer station, the second wireless transfer station can select a frequency for a wireless transfer coil of the second wireless transfer station to receive energy and/or data from the wireless transfer coil of the first wireless transfer station. In another embodiment, the second wireless transfer station can communicate the selected frequency information to the first wireless transfer station and receive energy from the wireless transfer coil of the first wireless transfer station at the wireless transfer coil of the second wireless transfer station on the selected frequency. In one embodiment, the first wireless transfer station and/or the second wireless transfer station can change the frequency of a wireless transfer coil using a variable capacitor, a variable inductor, a variable resistor, an impedance matching switch, and so forth.

Figure 19:
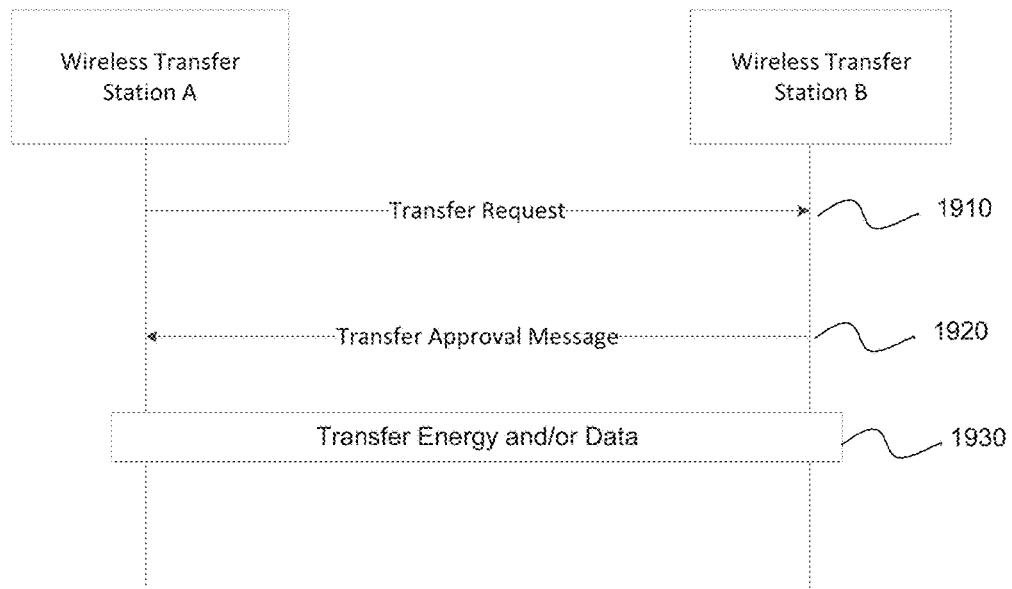
FIG. 19 shows a framework for a wireless transfer station in communication with another wireless transfer station to determine when to transfer wireless energy and/or data between the wireless transfer stations in accordance with an example.

FIG. 19 shows a wireless transfer station A in communication with wireless transfer station B to determine when to transfer wireless energy and/or data between wireless transfer station A and wireless transfer station B. In one embodiment, wireless transfer station A can send a transfer request to a wireless transfer station B, as in block 1910. In one embodiment, the transfer request can include a frequency capability of the wireless transfer station A. In another embodiment, the wireless transfer station B can send a transfer approval message with a frequency for transferring energy and/or data to the wireless transfer station A, as in block 1920. In another embodiment, the wireless transfer station A and the wireless transfer station B can transfer energy and/or data between wireless transfer station A and wireless transfer station B using the frequency indicated in the transfer approval message, as in block 1930.

Figure 20:
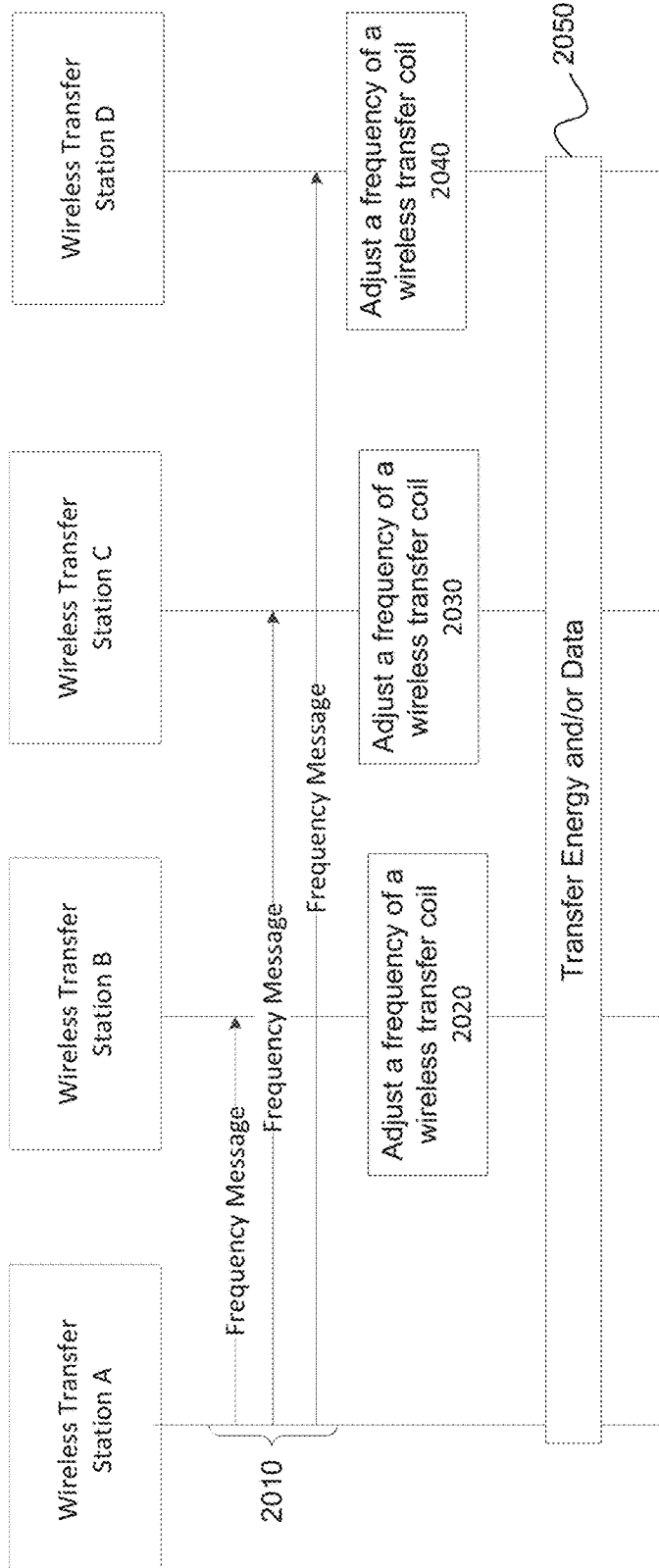
FIG. 20 shows a framework for a wireless transfer station in communication with a plurality of wireless transfer stations to determine when to transfer wireless energy and/or data between the wireless transfer station and one or more of the plurality of wireless transfer stations in accordance with an example.

FIG. 20 shows a wireless transfer station A in communication with a plurality of wireless transfer stations (e.g. wireless transfer station B, wireless transfer station C, and wireless transfer station D) to determine when to transfer wireless energy and/or data between wireless transfer station A and one or more of the plurality of wireless transfer stations. In one embodiment, the wireless transfer station A can broadcast or unicast to the wireless transfer station B, the wireless transfer station C, and/or the wireless transfer station D a frequency message that includes one or more frequencies the wireless transfer station B, the wireless transfer station C, and/or the wireless transfer station D to use to receive energy and/or data, as in block 2010. In one embodiment, when the wireless transfer station B, the wireless transfer station C, and/or the wireless transfer station D receive the frequency message, each of the wireless transfer stations B, C, and/or D can adjust a frequency of a wireless transfer coil coupled each of the wireless transfer stations B, C, and/or D for transferring energy and/or data, as in blocks 2020, 2030, and 2040. In another embodiment, the wireless transfer stations A, B, C, and/or D can dynamically adjust the frequency for transferring energy and/or data using an active crystal array to produce different frequency signals. In another embodiment, the wireless transfer station A and the wireless transfer station B, the wireless transfer station C, and/or the wireless transfer station D can transfer energy and/or data between the wireless transfer station A and the wireless transfer station B, the wireless transfer station C, and/or the wireless transfer station D using the one or more frequencies in the frequency message, as in block 2050.

Figure 21:
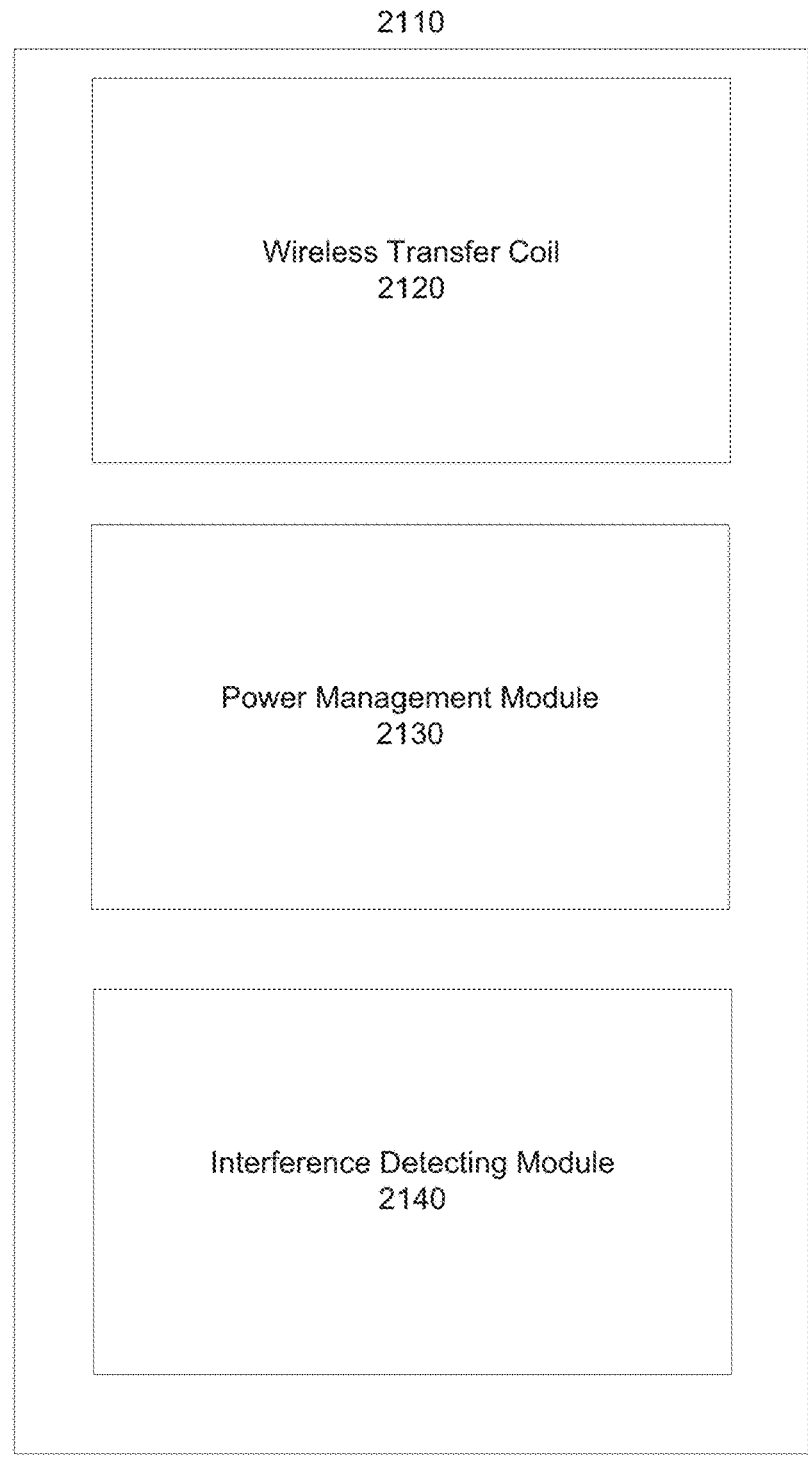
FIG. 21 depicts a wireless transfer station in accordance with an example.

FIG. 21 shows a wireless transfer station 2110 that can include: a wireless transfer coil 2120, a power management module 2130, and an interference-detecting module 2140. In one embodiment, the interference-detecting module 2140 can determine that the wireless transfer station 2110 is causing interference with a communications device. In another embodiment, the interference-detecting module 2140 can determine when the device or an object is interfering with a wireless transfer of energy or data between the wireless transfer station 2110 and another wireless transfer station or device. In one example, when the interference detecting module 2140 detects interference with the transfer of energy or data, the wireless transfer station 2110 can increase or decrease an energy and/or data transmission level of the wireless transfer station 2110, increase or decrease an energy transfer coverage scope of the wireless transfer station 2110, redirect transmitted energy to another location, switch to using one or more other wireless transfer coils for energy and/or data transfers, temporarily stop transferring energy and/or data, communicate or display an interference indicator to a user, and so forth.

In one example, a first wireless transfer station can transfer energy and/or data on a plurality of frequencies at the same time. In this example, when a second wireless transfer station detects interference using an interference-detecting module 2140 on a frequency for receiving wireless energy from the first wireless transfer station, the second wireless transfer station can switch to another frequency with a decreased amount of interference. In another embodiment, the first wireless transfer station and/or the second wireless transfer station can determine an amount of interference at one or more frequencies by comparing an actual amount of energy received at the second wireless transfer station for a selected frequency with an estimated amount of energy and/or data to be received at the second wireless transfer station for the selected frequency.

In one embodiment, a wireless transfer station can use a plurality of resonant frequencies to transfer energy to one or more devices or one or more other wireless transfer stations. In another embodiment, the wireless transfer station can provide different amounts of energy to different devices or other wireless transfer stations at different resonant frequencies. In one example, a first wireless transfer station can receive wireless energy from a primary wireless transfer station at a first resonant frequency and a second wireless transfer station can receive wireless energy from the primary wireless transfer station at a second resonant frequency.

In one embodiment, the primary wireless transfer station can set priority levels for the different devices or other wireless transfer stations receiving wireless energy at different resonant frequencies. In one example, a first wireless transfer station with a highest priority can receive wireless energy from the primary wireless transfer station at a first selected resonant frequency and a second wireless transfer station with a lower priority can receive wireless energy from the primary wireless transfer station at a second selected resonant frequency.

In one embodiment, the primary wireless transfer station may not have the capability to provide wireless energy to all the devices and/or other wireless transfer stations requesting wireless energy transfer. When the primary wireless transfer station does not have the capability to support all of the and/or other wireless transfer stations requesting wireless transfer requesting wireless energy transfer, the primary wireless transfer station can transfer energy to selected devices based on an energy transfer priority. In one embodiment, the primary wireless transfer station can select different resonant frequencies to transfer energy to different devices based on the energy transfer priority of the device. In one example, the primary wireless transfer station can be capable of supporting energy transfer for a combination of up to 5 devices and/or other wireless transfer stations and 10 devices and other wireless transfer stations can request wireless energy transfer. In this example, the primary wireless transfer station can determine the priority of the 10 devices and/or other wireless transfer stations and select 5 devices and/or other wireless transfer stations to transfer energy to. The primary wireless transfer station can select one or more resonant frequencies to transfer energy to the 5 devices. The remaining devices can be de-selected (e.g. not selected) for charging by not tuning transmitting coils to frequencies of the remaining devices. In one embodiment, the remaining devices can be selected and charged after the first 5 have been charged.

In one embodiment, a transmission frequency of a wireless transfer coil of a wireless transfer station for transferring wireless energy can be based on a natural frequency of the wireless transfer station, a device, and/or a wireless transfer coil wireless of another wireless transfer station.

In one embodiment, the wireless transfer station can include a load-sensing module to detect the presence or absence of an object in a selected area adjacent to the wireless transfer station that resonates at one or more selected frequencies. In one example, the load-sensing module can monitor a load, such as a current load, on the wireless transfer station. The load on the wireless transfer station can be affected by the presence or absence of objects in selected areas adjacent the wireless transfer station that resonate at one or more frequencies that the wireless transfer station is using to transfer energy.

In one embodiment, changes in the load of the wireless transfer station can be monitored by the load-sensing module and used to determine when an object, such as a living being or electrically conductive object, is in a selected area adjacent to the wireless transfer station. In one embodiment, when a change in a load is detected, the wireless transfer station can stop transferring wireless energy. In another embodiment, when a change in load is detected the wireless transfer station can switch the resonant frequency on which the energy is transferred. In another embodiment, when a change in load is detected, the wireless transfer station can determine that a device or object with a receiving coil capable of receiving energy at the selected resonant frequency has entered the selected area. In another embodiment, when the wireless transfer station determines that a human being is in the electromagnetic field emitted by the wireless transfer station, the wireless transfer station can dynamically and/or actively steer the transmitted wireless energy to avoid the human being.

Figure 22:
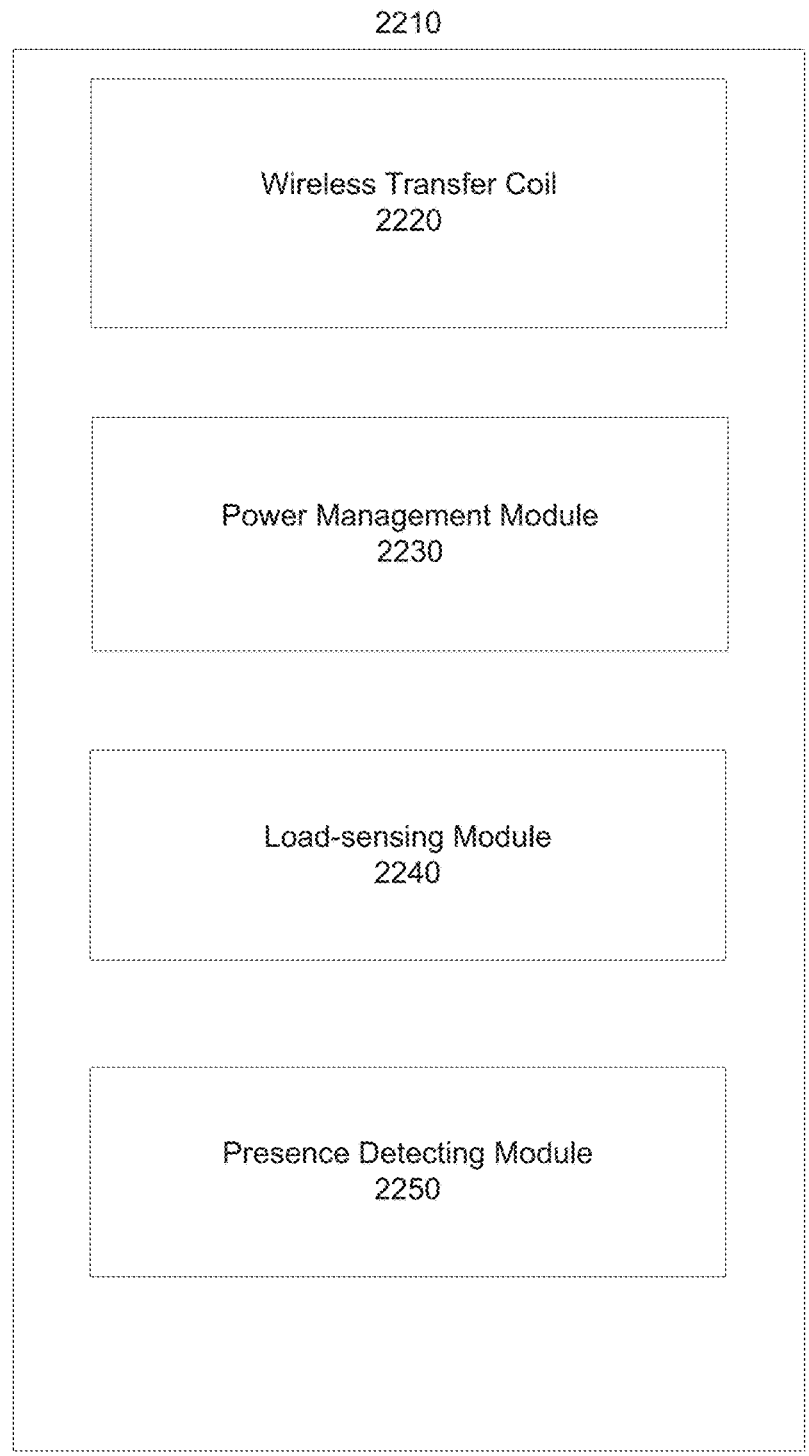
FIG. 22 depicts another wireless transfer station in accordance with an example.

FIG. 22 shows a wireless transfer station 2210 that can include: a wireless transfer coil 2220, a power management module 2230, a load-sensing module 2240, and a presence detecting module 2250. In one embodiment, the load-sensing module 2240 can be coupled to the wireless transfer coil 2220 of the wireless transfer station 2210 or a wireless transfer coil separate from the wireless transfer station. In another embodiment, the load-sensing module 2240 can detect a change of a load on the wireless transfer coil 2220. In one embodiment, one or more of load sensing modules 2240 can be coupled to the wireless transfer station 2210 or in communication with the wireless transfer station 2210 from selected locations.

In one embodiment, the wireless transfer station 2210 can monitor for a change in one or more loads detected by one or more load sensing modules 2240 to determine a location of an object relative to at least one of the one or more load sensing modules 2240. In another embodiment, the wireless transfer station 2210 can monitor for a change in one or more loads detected by one or more load sensing modules 2240 to determine a frequency that an object absorbs transmitted energy and/or data. In one embodiment, the wireless transfer station 2210 can track and/or store load information from one or more of the load sensing modules 2240. In one embodiment, the wireless transfer station 2210 can use a load-sensing module 2240 to detect the presence of an object in a select area or location. In one example for a hospital environment, the wireless transfer station 2210 can use a load-sensing module 2240 to detect when a patient has entered a selected location within the hospital. In another example for a hospital environment, the wireless transfer station 2210 can use the load-sensing module 2240 to detect when a patient has left a selected location within the hospital.

In one embodiment, the wireless transfer station 2210 can use one or more load sensing modules 2240 and/or one or more presence detectors 2250 to monitor a presence of an object at a selected location or area and/or monitor as an object approaches the selected location or area. In another embodiment, the wireless transfer station 2210 can cease a wireless energy and/or data transfer and/or change a wireless energy and/or data transfer frequency when an object is within a threshold distance from the selected location or area.

Figure 23:
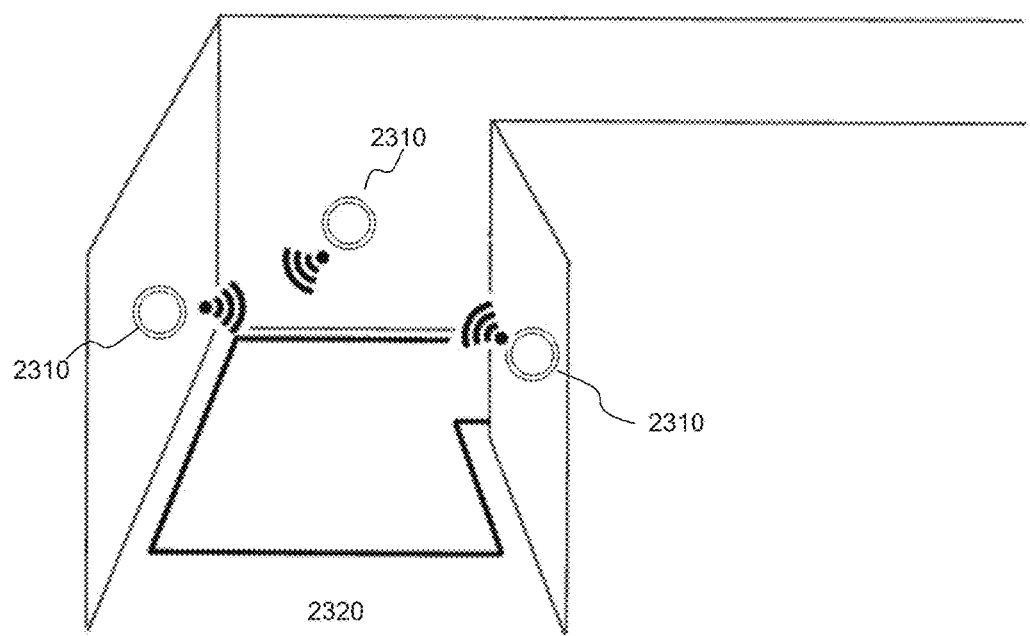
FIG. 23 depicts a plurality of presence detectors at selected locations to detect a presence of an object in a select area or location in accordance with an example.

FIG. 23 shows a plurality of presence detectors 2310 at selected locations to detect a presence of an object in a select area or location. In one embodiment, the presence detector 2310 can determine when an object enters a selected location and/or is located within a selected distance of the selected location. In one embodiment, the presence detector 2310 can be an infrared detector, a motion detector, a thermal sensor, an image sensor, a video sensor, and so forth. In one embodiment, the presence detectors 2310 can be located in a medical facility, such as a hallway 2320. In another embodiment, the presence detectors 2310 can be coupled to a wireless transfer device. In another embodiment, the presence detectors 2310 can be in communication with a wireless transfer device.

In selected environments, there can be transfer thresholds limiting an amount of energy and/or data that a wireless transfer station can transfer and/or a selected frequency at which the wireless transfer station can transfer energy and/or data. In one example, a transfer threshold can limit an amount of electromagnetic radiation absorbed by a living being. In another example, the wireless transfer station can be located in an environment in areas not occupied by humans, or occupied infrequently by humans where there is not a transfer threshold amount of energy and/or data that can be transferred and/or a frequency at which the energy and/or data can be transferred, such as a storage area, a basement, and so forth. In one embodiment, the wireless transfer station can increase an energy output transmission level above a selected transfer threshold when the wireless transfer station is located in an environment that is not currently occupied by living beings.

In one embodiment, the wireless transfer station can determine a transfer threshold based on the location of the wireless transfer station and decrease an energy transfer output level and/or a transfer frequency of the wireless transfer station below the transfer threshold. In another embodiment, when the transfer threshold is based on the presence of an object, such as a living being, the wireless transfer station can transfer the energy and/or data at a first selected energy level and/or frequency when the object is not present and a second selected energy level and/or frequency when the object is present.

An object, such as a foreign object, can have one or more natural frequencies. A natural frequency can be a frequency at which the object naturally vibrates or oscillates and a frequency at which the object can naturally receive or absorb energy and/or data. In one embodiment, a wireless transfer station can scan a selected area to determine a natural frequency of one or more objects in the selected area. In another embodiment, the wireless transfer station can determine the least congested or crowded frequency to transfer energy and/or data to one or more selected wireless transfer stations. In another embodiment, the wireless transfer station can determine a frequency with a congestion level below a selected threshold to transfer energy and/or data to one or more selected wireless transfer stations. In another embodiment, when the wireless transfer station has selected a frequency for transferring energy and/or data to one or more selected wireless transfer stations, the wireless transfer station can broadcast or unicast the selected frequency to the one or more selected wireless transfer stations. In another embodiment, the one or more selected wireless transfer stations can be wireless transfer stations authorized to receive wireless energy and/or data or wireless transfer stations requesting energy and/or data transfer.

In one embodiment, the wireless transfer station can detect when objects enter a coverage area of the wireless transfer station, such as by using a load-sensing module and/or a presence detecting module discussed in the preceding paragraphs. In another embodiment, the wireless transfer station can store one or more predetermined frequencies for different types of objects. In one example, when an object with a selected predetermined frequency enters the coverage area of the wireless transfer station, the wireless transfer station can stop transferring energy and/or data at the selected predetermined frequency. In another embodiment, when an object with a selected predetermined frequency value enters the coverage area, the wireless transfer station can switch to another frequency to transfer energy and/or data to one or more devices and/or one or more wireless transfer stations.

In one embodiment, the wireless transfer station can include a motion detector. In another embodiment, when the motion detector detects movement of an object within a selected distance of the wireless transfer station, the wireless transfer station can stop transferring energy. In one example, when the motion detector detects movement of an object within a selected distance of the wireless transfer station, the wireless transfer station can determine whether the moving object is absorbing energy and/or data at a selected frequency. In another example, when the moving object is absorbing energy and/or data at the selected frequency, the wireless transfer station can stop transferring energy and/or data at the selected frequency or switch to another frequency. In another example, the wireless transfer station can determine a type of object within a selected distance of the wireless transfer station and perform a selected activity based on the type of object. In one embodiment, the selected activity can include: ceasing transferring wireless energy and/or data, reducing a transmitting level of the wireless transfer station, or changing a frequency used to transfer wireless energy and/or data.

In one embodiment, when a wireless transfer station that is transmitting wireless energy using a magnetic field can adjust a shape or a form a magnetic field using beamforming and/or field shaping.

Figure 24:
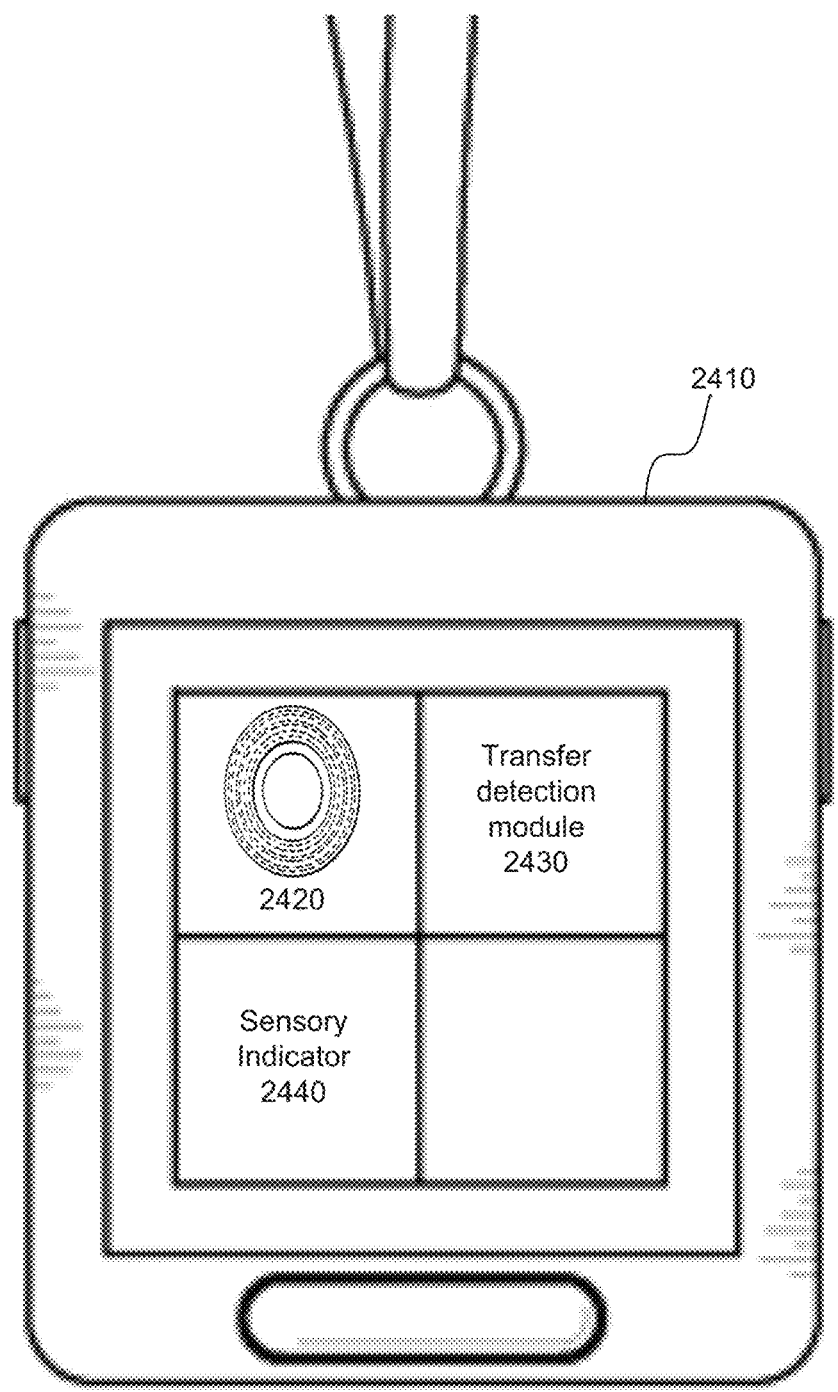
FIG. 24 depicts an exemplary embodiment of a wireless transfer station configured to be a wireless transfer safety gauge in accordance with an example.

FIG. 24 shows an exemplary embodiment of a wireless transfer station configured to be a wireless transfer safety gauge 2410. In another embodiment, the wireless transfer safety gauge 2410 can include a wireless transfer coil 2420 and a transfer detection module 2430. In another embodiment, the wireless transfer safety gauge 2410 can be attached to an individual or a device. In another embodiment, the wireless transfer safety gauge 2410 can be a wearable device, such as a keychain, wristband, badge, and so forth, which can attach to a user. In one example, the wireless transfer safety gauge 2410 can use the wireless transfer coil 2420 to detect an amount of wireless energy and/or data being transferred at a selected location by one or more other wireless transfer stations or one or more devices.

In one embodiment, when the wireless transfer safety gauge 2410 receives an amount of wireless energy and/or data using the wireless transfer coil 2420, the transfer detection module 2430 can determine that the amount of received wireless energy and/or data exceeds a selected threshold. In another embodiment, when the transfer detection module 2430 determines that the selected threshold is exceeded, the wireless transfer safety gauge 2410 can alert a user and/or a third party. In another embodiment, the wireless transfer safety gauge 2410 can include a sensory indicator 2440 to alert the user and/or the third party. In one example, the sensory indicator can include: a display, such as a light emitting diode (LED) display, liquid crystal display (LCD), or a touch screen; a speaker; a vibrating device; and so forth.

In one example, a medical professional or a patient at a medical facility can wear the wireless transfer safety gauge 2410 to detect when the medical professional or the patient is at a location where the medical professional or the patient is absorbing wireless energy above the selected threshold level. One advantage of the wireless transfer safety gauge 2410 is that the wireless transfer safety gauge 2410 can alert an individual or a third party when the individual is in a location where the individual is absorbing wireless energy beyond a safety threshold. In one example, when the wireless transfer safety gauge 2410 alerts the individual or the third party that a safety threshold for wireless energy absorption has been exceeded, the individual can move or be moved to a location where a level of wireless energy is below a safety threshold amount. In another embodiment, the wireless transfer safety gauge 2410 can display and/or provide a sensory alert of an amount of wireless energy that the wireless transfer safety gauge 2410 is currently receiving or has previously received.

Figure 25:
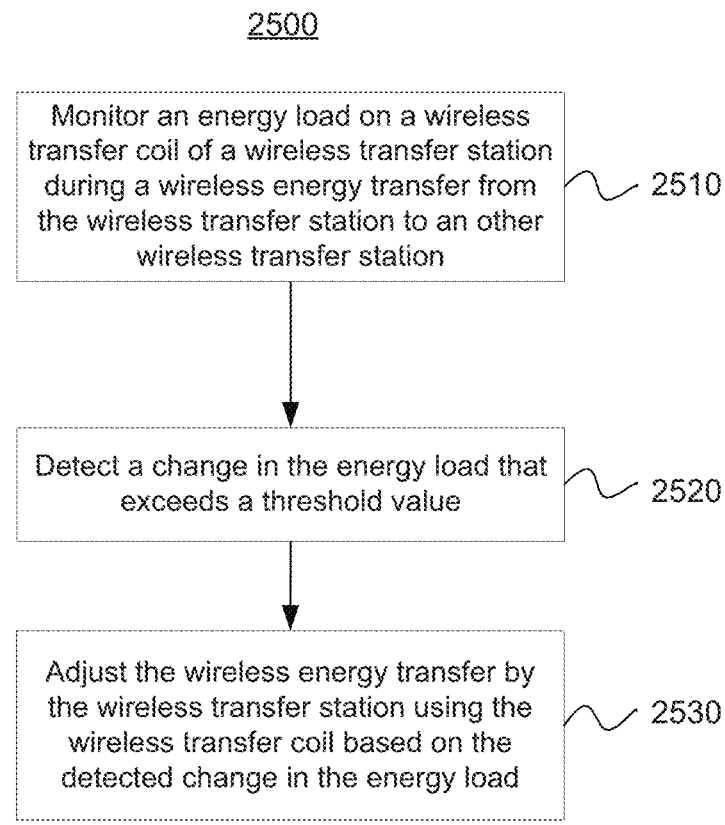
FIG. 25 shows a flow chart illustrating a functionality of a wireless interference detection device operable to detect interference during a wireless energy transfer between wireless transfer stations in accordance with an example.

FIG. 25 uses a flow chart 2500 to illustrate the functionality of one embodiment of the wireless interference detection device operable to detect interference during a wireless energy transfer between wireless transfer stations. The functionality may be implemented as a method or the functionality may be executed as instructions on a machine, where the instructions are included on at least one computer readable medium or one non-transitory machine readable storage medium. The wireless interference detection device can be configured to monitor an energy load on a wireless transfer coil of a wireless transfer station during a wireless energy transfer from the wireless transfer station to another wireless transfer station, as in block 2510. The wireless interference detection device can be further configured to detect a change in the energy load that exceeds a threshold value, as in block 2520. The wireless interference detection device can be further configured to adjust the wireless energy transferred by the wireless transfer station using the wireless transfer coil based on the detected change in the energy load, as in block 2530.

In one embodiment, the interference is caused by a foreign object within a magnetic field of the wireless transfer coil. In another embodiment, the interference is caused by a radio transmission from a device. In another embodiment, the wireless energy interference device of can be further configured to receive energy consumption information from a device receiving wireless energy from the wireless transfer station and determine when the detected change in the energy load is caused by the device receiving energy from the wireless transfer coil of the wireless transfer station. In another embodiment, the wireless energy interference device can be further configured to cease transferring energy when the change in the energy load exceeds a threshold value.

In one embodiment, the wireless energy interference device can be further configured to determine when the change in energy load is caused by a foreign object entering into an electromagnetic field transmitted from the wireless transfer coil. In another embodiment, the wireless energy interference device can be further configured to adjust a wireless energy transmission frequency of the wireless transfer coil when the foreign object is detected. In another embodiment, the wireless energy interference device can be further configured to determine a location of the wireless energy interference device or the wireless transfer station and adjust an amount of wireless energy transferred by the wireless transfer station based on the detected change in the energy load and the location of the wireless energy interference device or the wireless transfer station.

In one embodiment, the wireless energy interference device can be further configured to adjust an amount of wireless energy transferred to the other wireless transfer station using the wireless transfer coil based on selected energy transfer criteria. In another embodiment, the selected energy transfer criteria can include: a predetermined location-based wireless energy transfer level threshold; a number of foreign objects within a selected distance from the wireless transfer coil; a type of foreign object within a selected distance from the wireless transfer coil; a time of day; and/or a day of a week.

Figure 26:
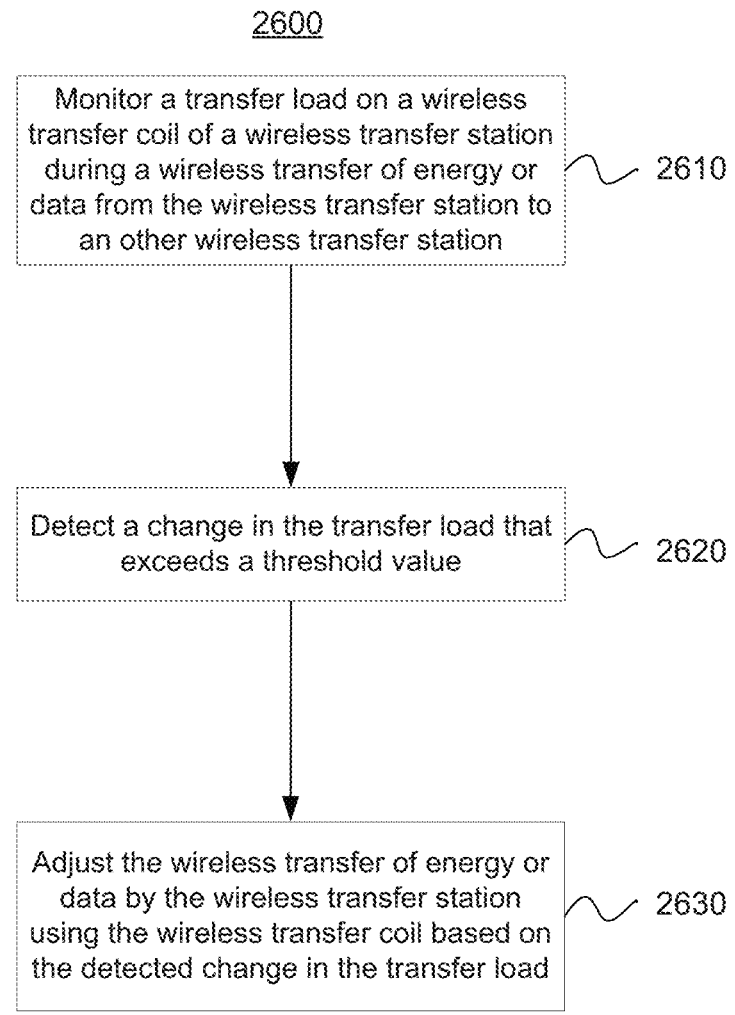
FIG. 26 shows a flow chart illustrating a functionality of a wireless transfer station operable to detect interference during a wireless transfer of energy or data between wireless transfer stations in accordance with an example.

FIG. 26 uses a flow chart 2600 to illustrate the functionality of one embodiment of the wireless transfer station operable to detect interference during a wireless transfer of energy or data between wireless transfer stations. The functionality may be implemented as a method or the functionality may be executed as instructions on a machine, where the instructions are included on at least one computer readable medium or one non-transitory machine readable storage medium. The wireless transfer station can be configured to detect interference during a wireless transfer of energy or data between wireless transfer stations, as in block 2610. The wireless transfer station can be further configured to detect a change in the transfer load that exceeds a threshold value, as in block 2620. The wireless transfer station can be further configured to adjust the wireless transfer of energy or data by the wireless transfer station using the wireless transfer coil based on the detected change in the transfer load, as in block 2630.

In one embodiment, the wireless transfer station can be further configured to determine a frequency or a natural frequency of a foreign object within a selected distance from the wireless transfer coil or the wireless transfer station. In another embodiment, the wireless transfer station can be further configured to determine a type of the foreign object based on the frequency or the natural frequency of the foreign object. In another embodiment, the type of the foreign object includes: organic material; a human; a conductive object; and/or a metal object. In another embodiment, the wireless transfer station can be further configured to detect a foreign object within a selected distance of an electromagnetic field created by the wireless transfer coil of the wireless transfer station for transferring energy or data and dynamically adjust an amount of wireless energy or data transferred by the wireless transfer station using the wireless transfer coil when the foreign object is detected. In another embodiment, the wireless transfer station can be further configured to switch to a different transfer frequency when a foreign object is detected by the wireless transfer station.

In one embodiment, the wireless transfer station can be further configured to detect the presence of a foreign object using an object presence detecting sensor. In another embodiment, the wireless transfer station can be further configured to detect the presence of a foreign object at a distance that exceeds a range of an electromagnetic field created by the wireless transfer coil by using an object presence detecting sensor. In another embodiment, the object presence detecting sensor includes an ultrasonic sensor, a motion detection sensor, a laser sensor, an infrared sensor, a thermal heat sensor, a thermal imaging sensor, a video sensor, a photo detector, an imaging sensor, a sonar sensor, a gyroscope, and/or a microphone. In another embodiment, the wireless transfer station can be further configured to communicate object presence information with one or more other wireless transfer stations and determine a location of a foreign object within an electromagnetic field of the one or more other wireless transfer stations.

Figure 27:
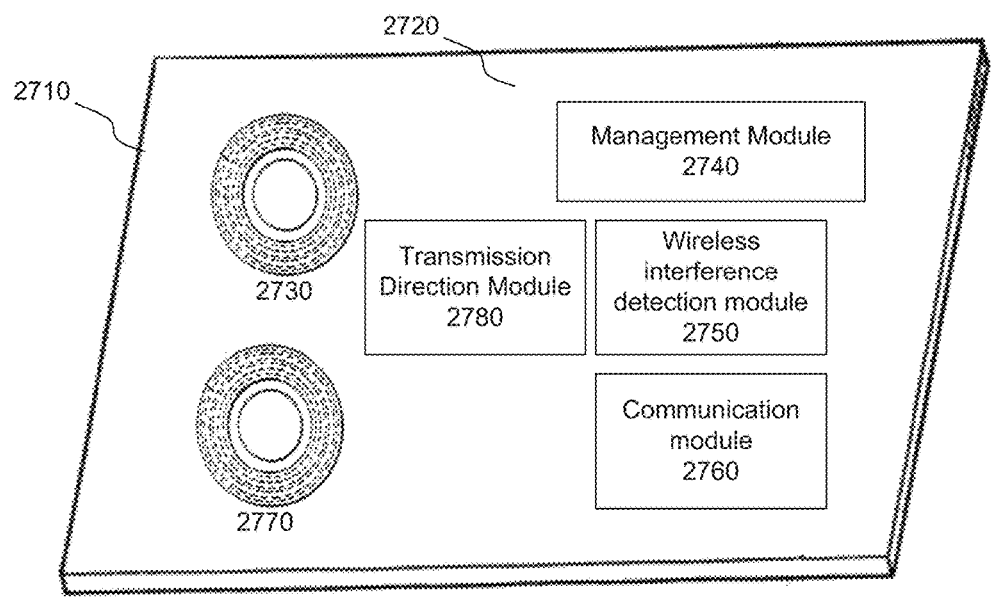
FIG. 27 depicts a wireless transfer station operable to transfer energy or data in accordance with an example.

FIG. 27 shows a wireless transfer station 2710 operable to transferring wireless energy, the wireless transfer station 2710 comprising: a transfer platform 2720 having at least one surface for wirelessly transferring energy or data with another wireless transfer station; a wireless transfer coil 2730 located within the transfer platform 2720; a management module 2340 for controlling the wireless transfer coil 2730; and a wireless interference detection module 2350 for detecting interference in an electromagnetic field used by the wireless transfer station 2710 to wirelessly transfer energy or data.

In one embodiment, the wireless transfer station 2710 can further comprise a communication module 2760 configured to communicate information between the wireless transfer station 2710 and a device. In another embodiment, the communication module can be further configured to send an alert to a user of the wireless transfer station or a third party when interference is detected during the wireless transfer of energy or data. In another embodiment, the communication module can be further configured to receive interference information from the other device and determine when the wireless transfer of energy or data affects cellular communication or a wireless communication by the other device.

In one embodiment, the wireless transfer station can further comprise a plurality of wireless transfer coils, wherein the wireless interference detection module is further configured to detect interference with the wireless transfer of energy or data and the management module is further configured to switch from a wireless transfer coil of the plurality of wireless transfer coils currently used for the wireless transfer of energy or data to a different wireless transfer coil of the plurality of wireless transfer coils for the wireless transfer of energy or data. In another embodiment, the wireless transfer station can further comprise a transmission direction module to direct a path of the wireless transfer of energy or data, wherein the transmission direction module is configured to redirect the path of the wireless energy or data transfer when the wireless interference detection module detects interference with the wireless transfer of energy or data. In another embodiment, the wireless interference detection module can be further configured to detect interference from an object and adjust a frequency of the wireless transfer coil used to wirelessly transfer energy or data.

Figure 28:
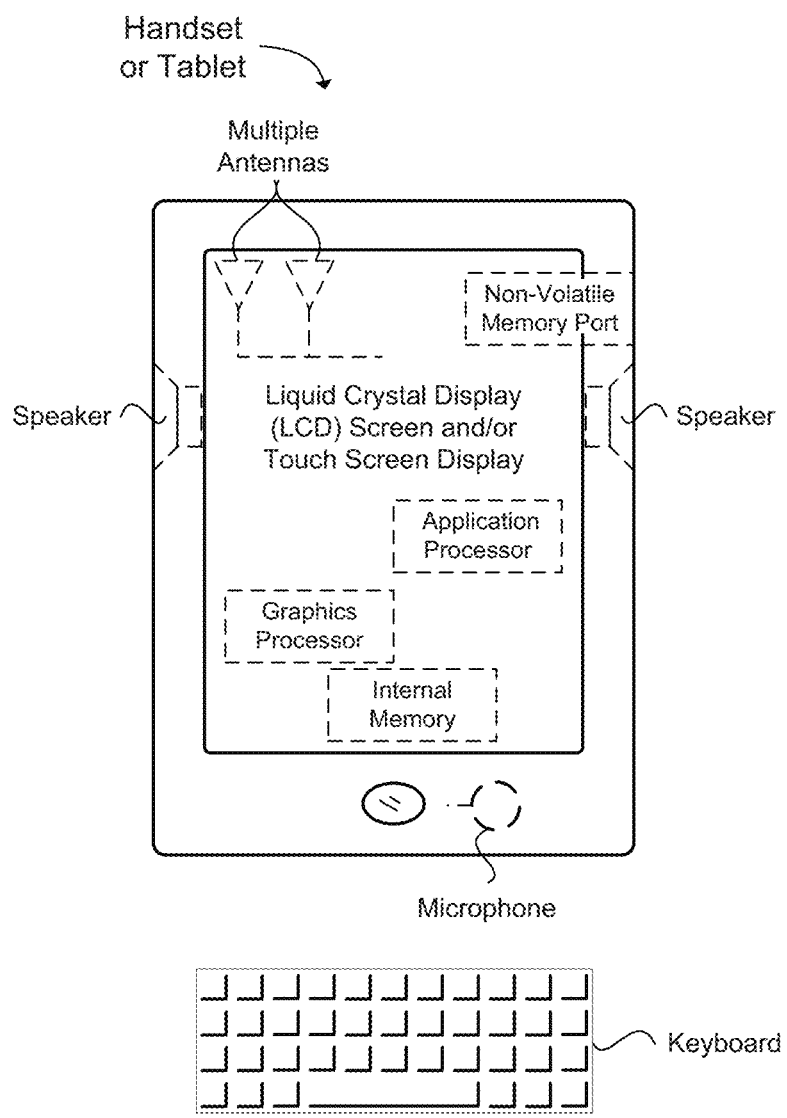
FIG. 28 illustrates a diagram of a device in accordance with an example.

FIG. 28 provides an example illustration of the device, such as a user equipment (UE), a mobile station (MS), a mobile wireless device, a mobile communication device, a tablet, a handset, or other type of device. The device can include one or more antennas configured to communicate with a node or transmission station, such as a base station (BS), an evolved Node B (eNode B), a baseband unit (BBU), a remote radio head (RRH), a remote radio equipment (RRE), a relay station (RS), a radio equipment (RE), a remote radio unit (RRU), a central processing module (CPM), or other type of wireless wide area network (WWAN) access point. The device can be configured to communicate using at least one wireless communication standard including 3GPP LTE, WiMAX, High Speed Packet Access (HSPA), Bluetooth, and Wi-Fi. The device can communicate using separate antennas for each wireless communication standard or shared antennas for multiple wireless communication standards. The device can communicate in a wireless local area network (WLAN), a wireless personal area network (WPAN), and/or a WWAN.

FIG. 28 also provides an illustration of a microphone and one or more speakers that can be used for audio input and output from the device. The display screen may be a liquid crystal display (LCD) screen, or other type of display screen such as an organic light emitting diode (OLED) display. The display screen can be configured as a touch screen. The touch screen may use capacitive, resistive, or another type of touch screen technology. An application processor and a graphics processor can be coupled to internal memory to provide processing and display capabilities. A non-volatile memory port can also be used to provide data input/output options to a user. The non-volatile memory port may also be used to expand the memory capabilities of the device. A keyboard may be integrated with the device or wirelessly connected to the device to provide additional user input. A virtual keyboard may also be provided using the touch screen.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or other medium for storing electronic data. The base station and mobile station may also include a transceiver module, a counter module, a processing module, and/or a clock module or timer module. One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as defacto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of layouts, distances, network examples, etc., to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A wireless transfer station operable to transferring wireless energy, the wireless transfer station comprising:
   a transfer platform having at least one surface for wirelessly transferring energy or data with another wireless transfer station;
   a wireless transfer coil located within the transfer platform;
   a management module for controlling the wireless transfer coil; and
   a wireless interference detection module for detecting interference in an electromagnetic field used by the wireless transfer station to wirelessly transfer energy or data, wherein the interference is a radio transmission from a device, and wherein the wireless transfer station is operable to adjust a frequency of the wireless transfer coil in response to the interference.

2. The wireless transfer station of claim 1, further comprising a communication module configured to communicate information between the wireless transfer station and a device.

3. The wireless transfer station of claim 2, wherein the communication module is further configured to send an alert to a user of the wireless transfer station or a third party when interference is detected during the wireless transfer of energy or data.

4. The wireless transfer station of claim 2, wherein the communication module is further configured to:
   receive interference information from the device; and
   determine when the wireless transfer of energy or data affects cellular communication or a wireless communication by the device.

5. The wireless transfer station of claim 1, further comprising:
   a plurality of wireless transfer coils, wherein
      the wireless interference detection module is further configured to detect interference with the wireless transfer of energy or data; and
      the management module is further configured to switch from a wireless transfer coil of the plurality of wireless transfer coils currently used for the wireless transfer of energy or data to a different wireless transfer coil of the plurality of wireless transfer coils for the wireless transfer of energy or data.

6. The wireless transfer station of claim 1, further comprising:
   a transmission direction module to direct a path of the wireless transfer of energy or data,
   wherein the transmission direction module is configured to redirect the path of the wireless energy or data transfer when the wireless interference detection module detects interference with the wireless transfer of energy or data.

7. The wireless transfer station of claim 1, wherein the wireless interference detection module is configured to:
   detect interference from an object; and
   adjust a frequency of the wireless transfer coil used to wirelessly transfer energy or data.

* * * * *